(12) United States Patent
Escutia et al.

(10) Patent No.: US 8,382,681 B2
(45) Date of Patent: Feb. 26, 2013

(54) FULLY INTEGRATED WEARABLE OR HANDHELD MONITOR

(75) Inventors: Raul Escutia, Daly City, CA (US);
Craig M. Litherland, Cupertino, CA (US); Jeffrey L. Emery, Redwood City, CA (US); James W. Pfeiffer, Los Gatos, CA (US); Christo P. Pamichev, Sunnyvale, CA (US)

(73) Assignee: Intuity Medical, Inc., Sunnyvale, CA (US)

( * ) Notice: Subject to any disclaimer, the term of this patent is extended or adjusted under 35 U.S.C. 154(b) by 201 days.

(21) Appl. No.: 11/529,612

(22) Filed: Sep. 29, 2006

(65) Prior Publication Data

US 2007/0179404 A1 Aug. 2, 2007

Related U.S. Application Data

(60) Provisional application No. 60/721,966, filed on Sep. 30, 2005.

(51) Int. Cl.
*A61B 5/00* (2006.01)

(52) U.S. Cl. .......................... 600/583; 33/512; 604/191

(58) Field of Classification Search .................. 600/583; 604/191; 33/512
See application file for complete search history.

(56) References Cited

U.S. PATENT DOCUMENTS

| | | | |
|---|---|---|---|
| 842,690 A | 1/1907 | Oswalt |
| D137,874 S | 5/1944 | Partridge |
| 2,749,797 A | 3/1950 | Harks |
| 3,092,465 A | 6/1963 | Adams, Jr. |
| 3,310,002 A | 3/1967 | Wilburn |
| 3,620,209 A | 11/1971 | Kravitz |
| 3,623,475 A | 11/1971 | Sanz et al. |
| 3,626,929 A | 12/1971 | Sanz et al. |
| 3,630,957 A | 12/1971 | Rey |
| D223,165 S | 3/1972 | Komendat |
| 3,723,064 A | 3/1973 | Liotta |
| 3,741,197 A | 6/1973 | Sanz et al. |
| 3,961,898 A | 6/1976 | Neeley et al. |
| 4,014,328 A | 3/1977 | Cluff et al. |
| 4,042,335 A | 8/1977 | Clement |
| 4,057,394 A | 11/1977 | Genshaw |
| 4,109,655 A | 8/1978 | Chacornac |
| 4,254,083 A | 3/1981 | Columbus |
| 4,258,001 A | 3/1981 | Pierce et al. |
| 4,260,257 A | 4/1981 | Neeley et al. |
| 4,289,459 A | 9/1981 | Neeley et al. |
| 4,321,397 A | 3/1982 | Nix et al. |
| 4,350,762 A | 9/1982 | DeLuca et al. |
| 4,394,512 A | 7/1983 | Batz |
| 4,414,975 A | 11/1983 | Ryder et al. |
| 4,418,037 A | 11/1983 | Katsuyama et al. |
| 4,422,941 A | 12/1983 | Vaughan, Jr. et al. |

(Continued)

FOREIGN PATENT DOCUMENTS

DE 199 22 413 A1 11/2000
DE 103 02 501 A1 8/2004

(Continued)

*Primary Examiner* — Max Hindenburg
*Assistant Examiner* — Renee Danega
(74) *Attorney, Agent, or Firm* — Morrison & Foerster LLP

(57) ABSTRACT

An arrangement comprises a housing containing one or more components configured for at least one of body fluid sampling and analysis. The arrangement includes a housing containing one or more components configured for at least one of body fluid sampling and analysis, and a body attachment element. The housing and the body attachment element are connected by a quick-release mechanism configured to facilitate removal of the housing from the body attachment element.

29 Claims, 17 Drawing Sheets

U.S. PATENT DOCUMENTS

| | | | |
|---|---|---|---|
| 4,429,700 A | 2/1984 | Thees et al. | |
| 4,627,445 A | 12/1986 | Garcia et al. | |
| 4,637,403 A * | 1/1987 | Garcia et al. | 600/583 |
| 4,637,406 A | 1/1987 | Guinn et al. | |
| 4,653,513 A | 3/1987 | Dombrowski | |
| 4,702,261 A | 10/1987 | Cornell et al. | |
| 4,711,250 A | 12/1987 | Gilbaugh, Jr. et al. | |
| 4,737,458 A | 4/1988 | Batz et al. | |
| 4,767,415 A | 8/1988 | Duffy | |
| 4,774,192 A | 9/1988 | Terminiello et al. | |
| 4,790,979 A | 12/1988 | Terminiello et al. | |
| 4,794,926 A | 1/1989 | Munsch et al. | |
| 4,815,843 A | 3/1989 | Tiefenthaler et al. | |
| 4,829,470 A | 5/1989 | Wang | |
| 4,846,785 A | 7/1989 | Cassou et al. | |
| 4,887,306 A | 12/1989 | Hwang et al. | |
| 4,920,977 A | 5/1990 | Haynes | |
| 4,930,525 A | 6/1990 | Palestrant | |
| 4,935,346 A | 6/1990 | Phillips et al. | |
| 4,953,552 A | 9/1990 | DeMarzo | |
| 4,966,646 A | 10/1990 | Zdeblick | |
| 4,995,402 A | 2/1991 | Smith et al. | |
| 5,029,583 A | 7/1991 | Meserol et al. | |
| 5,049,487 A | 9/1991 | Phillips et al. | |
| 5,050,617 A | 9/1991 | Columbus et al. | |
| 5,059,394 A | 10/1991 | Phillips et al. | |
| 5,077,199 A | 12/1991 | Basagni et al. | |
| 5,094,943 A | 3/1992 | Siedel et al. | |
| 5,116,759 A | 5/1992 | Klainer et al. | |
| 5,131,404 A | 7/1992 | Neeley et al. | |
| 5,141,868 A | 8/1992 | Shanks et al. | |
| 5,145,565 A | 9/1992 | Kater et al. | |
| 5,146,437 A | 9/1992 | Boucheron | |
| 5,153,416 A | 10/1992 | Neeley | |
| 5,164,575 A | 11/1992 | Neeley et al. | |
| 5,166,498 A | 11/1992 | Neeley | |
| 5,174,291 A | 12/1992 | Schoonen et al. | |
| 5,176,632 A | 1/1993 | Bernardi | |
| 5,179,005 A | 1/1993 | Phillips et al. | |
| 5,183,741 A | 2/1993 | Arai et al. | |
| 5,196,302 A | 3/1993 | Kidwell | |
| 5,208,163 A | 5/1993 | Charlton et al. | |
| 5,213,966 A | 5/1993 | Vuorinen et al. | |
| 5,217,480 A | 6/1993 | Habar et al. | |
| 5,218,966 A | 6/1993 | Yamasawa | |
| 5,223,219 A | 6/1993 | Subramanian et al. | |
| 5,234,818 A | 8/1993 | Zimmermann et al. | |
| 5,241,969 A | 9/1993 | Carson et al. | |
| 5,251,126 A | 10/1993 | Kahn et al. | |
| D341,848 S | 11/1993 | Bigelow et al. | |
| 5,275,159 A | 1/1994 | Griebel | |
| 5,278,079 A | 1/1994 | Gubinski et al. | |
| 5,288,646 A | 2/1994 | Lundsgaard et al. | |
| 5,299,571 A | 4/1994 | Mastrototaro | |
| 5,301,686 A | 4/1994 | Newman | |
| 5,302,513 A | 4/1994 | Miike et al. | |
| 5,304,468 A | 4/1994 | Phillips et al. | |
| 5,306,623 A | 4/1994 | Kiser et al. | |
| 5,308,767 A | 5/1994 | Terashima | |
| 5,320,607 A | 6/1994 | Ishibashi | |
| 5,354,537 A | 10/1994 | Moreno | |
| 5,360,595 A | 11/1994 | Bell et al. | |
| 5,368,047 A | 11/1994 | Suzuki et al. | |
| 5,383,512 A | 1/1995 | Jarvis | |
| 5,390,671 A | 2/1995 | Lord et al. | |
| 5,399,316 A | 3/1995 | Yamada | |
| 5,401,110 A | 3/1995 | Neeley | |
| 5,402,798 A | 4/1995 | Swierczek et al. | |
| 5,441,513 A | 8/1995 | Roth | |
| 5,451,350 A | 9/1995 | Macho et al. | |
| 5,458,140 A | 10/1995 | Eppstein et al. | |
| 5,460,777 A | 10/1995 | Kitajima et al. | |
| 5,460,968 A | 10/1995 | Yoshida et al. | |
| 5,482,473 A | 1/1996 | Lord et al. | |
| 5,506,200 A | 4/1996 | Hirschkoff et al. | |
| 5,507,288 A | 4/1996 | Böcker et al. | |
| 5,508,200 A | 4/1996 | Tiffany et al. | |
| 5,510,266 A | 4/1996 | Bonner et al. | |
| 5,514,152 A * | 5/1996 | Smith | 606/182 |
| 5,568,806 A | 10/1996 | Cheney, II et al. | |
| 5,569,287 A | 10/1996 | Tezuka et al. | |
| 5,575,403 A | 11/1996 | Charlton et al. | |
| 5,577,499 A | 11/1996 | Teves | |
| 5,582,184 A | 12/1996 | Erickson et al. | |
| 5,586,553 A | 12/1996 | Halili et al. | |
| 5,591,139 A | 1/1997 | Lin et al. | |
| 5,611,809 A | 3/1997 | Marshall et al. | |
| 5,624,458 A | 4/1997 | Lipscher | |
| 5,630,986 A | 5/1997 | Charlton et al. | |
| 5,632,410 A | 5/1997 | Moulton et al. | |
| 5,636,632 A | 6/1997 | Bommannan et al. | |
| 5,647,851 A | 7/1997 | Pokras | |
| 5,658,515 A | 8/1997 | Lee et al. | |
| 5,660,791 A | 8/1997 | Brenneman et al. | |
| 5,676,850 A | 10/1997 | Reed et al. | |
| 5,680,858 A | 10/1997 | Hansen et al. | |
| 5,681,484 A | 10/1997 | Zanzucchi et al. | |
| 5,682,233 A | 10/1997 | Brinda | |
| 5,697,901 A | 12/1997 | Eriksson | |
| 5,701,181 A | 12/1997 | Boiarski et al. | |
| 5,701,910 A | 12/1997 | Powles et al. | |
| 5,705,018 A | 1/1998 | Hartley | |
| 5,708,787 A | 1/1998 | Nakano et al. | |
| 5,715,417 A | 2/1998 | Gardien et al. | |
| 5,730,753 A | 3/1998 | Morita | |
| 5,735,273 A | 4/1998 | Kurnik et al. | |
| 5,736,103 A | 4/1998 | Pugh | |
| 5,741,211 A | 4/1998 | Renirie et al. | |
| 5,746,217 A | 5/1998 | Erickson et al. | |
| 5,746,720 A | 5/1998 | Stouder, Jr. | |
| 5,757,666 A | 5/1998 | Schreiber et al. | |
| 5,759,364 A | 6/1998 | Charlton et al. | |
| 5,766,066 A | 6/1998 | Ranniger | |
| 5,771,890 A | 6/1998 | Tamada | |
| 5,797,693 A | 8/1998 | Jaeger | |
| 5,801,057 A | 9/1998 | Smart et al. | |
| 5,807,375 A | 9/1998 | Gross et al. | |
| 5,820,570 A | 10/1998 | Erickson et al. | |
| 5,827,183 A | 10/1998 | Kurnik et al. | |
| 5,840,020 A | 11/1998 | Heinonen et al. | |
| 5,841,126 A | 11/1998 | Fossum et al. | |
| 5,843,692 A | 12/1998 | Phillips et al. | |
| 5,846,837 A | 12/1998 | Thym et al. | |
| 5,854,074 A | 12/1998 | Charlton et al. | |
| D403,975 S | 1/1999 | Douglas et al. | |
| 5,855,801 A | 1/1999 | Lin et al. | |
| 5,856,195 A | 1/1999 | Charlton et al. | |
| 5,858,194 A | 1/1999 | Bell | |
| 5,866,281 A | 2/1999 | Guckel et al. | |
| 5,871,494 A | 2/1999 | Simons et al. | |
| 5,879,310 A | 3/1999 | Sopp et al. | |
| 5,879,326 A | 3/1999 | Godshall et al. | |
| 5,879,367 A | 3/1999 | Latterell et al. | |
| 5,891,053 A | 4/1999 | Sesekura | |
| 5,893,870 A | 4/1999 | Talen et al. | |
| 5,911,711 A | 6/1999 | Pelkey | |
| 5,911,737 A | 6/1999 | Lee et al. | |
| 5,912,139 A | 6/1999 | Iwata et al. | |
| 5,925,021 A | 7/1999 | Castellano et al. | |
| 5,928,207 A | 7/1999 | Pisano et al. | |
| 5,930,873 A | 8/1999 | Wyser | |
| 5,938,679 A | 8/1999 | Freeman et al. | |
| 5,945,678 A | 8/1999 | Yanagisawa | |
| 5,951,492 A | 9/1999 | Douglas et al. | |
| 5,951,521 A | 9/1999 | Mastrototaro et al. | |
| 5,954,685 A | 9/1999 | Tierney | |
| 5,962,215 A | 10/1999 | Douglas et al. | |
| 5,968,760 A | 10/1999 | Phillips et al. | |
| 5,968,765 A | 10/1999 | Grage et al. | |
| 5,971,941 A | 10/1999 | Simons et al. | |
| 5,972,294 A | 10/1999 | Smith et al. | |
| 5,986,754 A | 11/1999 | Harding | |
| 5,989,409 A | 11/1999 | Kurnik et al. | |
| 5,993,189 A | 11/1999 | Mueller et al. | |
| 6,001,067 A | 12/1999 | Shults et al. | |
| 6,005,545 A | 12/1999 | Nishida et al. | |
| 6,010,463 A | 1/2000 | Lauks et al. | |

| | | | | | | | |
|---|---|---|---|---|---|---|---|
| 6,010,519 | A * | 1/2000 | Mawhirt et al. ............... 606/181 | 6,352,514 | B1 | 3/2002 | Douglas et al. |
| 6,014,135 | A | 1/2000 | Fernandes | 6,356,776 | B1 | 3/2002 | Berner et al. |
| 6,014,577 | A | 1/2000 | Henning et al. | 6,358,265 | B1 * | 3/2002 | Thorne et al. ............... 606/181 |
| 6,023,629 | A | 2/2000 | Tamada | 6,364,890 | B1 | 4/2002 | Lum et al. |
| 6,027,459 | A | 2/2000 | Shain et al. | 6,375,626 | B1 | 4/2002 | Allen et al. |
| 6,030,827 | A | 2/2000 | Davis et al. | 6,375,627 | B1 | 4/2002 | Mauze et al. |
| 6,032,059 | A | 2/2000 | Henning et al. | 6,379,969 | B1 | 4/2002 | Mauze et al. |
| 6,036,924 | A | 3/2000 | Simons et al. | 6,391,005 | B1 | 5/2002 | Lum et al. |
| 6,041,253 | A | 3/2000 | Kost et al. | 6,409,679 | B2 | 6/2002 | Pyo |
| 6,050,988 | A | 4/2000 | Zuck | 6,428,664 | B1 * | 8/2002 | Bhullar et al. ........... 204/403.03 |
| 6,056,701 | A | 5/2000 | Duchon et al. | 6,449,608 | B1 | 9/2002 | Morita et al. |
| 6,056,734 | A | 5/2000 | Jacobsen et al. | 6,455,324 | B1 | 9/2002 | Douglas |
| 6,058,321 | A | 5/2000 | Swayze et al. | 6,500,134 | B1 | 12/2002 | Cassone |
| 6,059,815 | A | 5/2000 | Lee et al. | 6,520,973 | B1 | 2/2003 | McGarry |
| 6,061,128 | A | 5/2000 | Zweig et al. | 6,530,892 | B1 | 3/2003 | Kelly |
| 6,063,039 | A | 5/2000 | Cunningham et al. | 6,537,243 | B1 | 3/2003 | Henning et al. |
| 6,071,251 | A | 6/2000 | Cunningham et al. | 6,540,675 | B2 | 4/2003 | Aceti et al. |
| 6,071,294 | A | 6/2000 | Simons et al. | 6,544,475 | B1 | 4/2003 | Douglas et al. |
| 6,077,660 | A | 6/2000 | Wong et al. | 6,555,061 | B1 | 4/2003 | Leong et al. |
| 6,080,116 | A | 6/2000 | Erickson et al. | 6,558,624 | B1 | 5/2003 | Lemmon et al. |
| 6,083,196 | A | 7/2000 | Trautman et al. | 6,579,690 | B1 | 6/2003 | Bonnecaze et al. |
| 6,086,544 | A | 7/2000 | Hibner et al. | 6,602,205 | B1 | 8/2003 | Erickson et al. |
| 6,090,790 | A | 7/2000 | Eriksson | 6,612,111 | B1 | 9/2003 | Hodges et al. |
| 6,091,975 | A | 7/2000 | Daddona et al. | 6,616,616 | B2 | 9/2003 | Fritz et al. |
| 6,093,156 | A | 7/2000 | Cunningham et al. | 6,626,874 | B1 | 9/2003 | Duchamp |
| 6,097,831 | A | 8/2000 | Wieck et al. | 6,656,167 | B2 | 12/2003 | Numao et al. |
| 6,099,484 | A | 8/2000 | Douglas et al. | 6,706,049 | B2 | 3/2004 | Moerman |
| 6,100,107 | A | 8/2000 | Lei et al. | 6,706,159 | B2 | 3/2004 | Moerman et al. |
| 6,102,933 | A | 8/2000 | Lee et al. | 6,740,800 | B1 * | 5/2004 | Cunningham ............... 84/423 R |
| 6,103,033 | A | 8/2000 | Say et al. | 6,748,275 | B2 | 6/2004 | Lattner et al. |
| 6,103,197 | A | 8/2000 | Werner | 6,753,187 | B2 | 6/2004 | Cizdziel et al. |
| 6,106,751 | A | 8/2000 | Talbot et al. | 6,766,817 | B2 | 7/2004 | da Silva |
| 6,118,126 | A | 9/2000 | Zanzucchi | 6,793,633 | B2 | 9/2004 | Douglas et al. |
| 6,120,676 | A | 9/2000 | Heller et al. | 6,830,669 | B2 | 12/2004 | Miyazaki et al. |
| 6,123,861 | A | 9/2000 | Santini, Jr. et al. | 6,836,678 | B2 | 12/2004 | Tu |
| 6,126,899 | A | 10/2000 | Woudenberg et al. | 6,837,858 | B2 | 1/2005 | Cunningham et al. |
| 6,132,449 | A | 10/2000 | Lum et al. | 6,847,451 | B2 | 1/2005 | Pugh |
| 6,139,562 | A | 10/2000 | Mauze et al. | 6,918,404 | B2 | 7/2005 | Dias da Silva |
| 6,142,939 | A | 11/2000 | Eppstein et al. | 6,919,960 | B2 | 7/2005 | Hansen et al. |
| 6,152,942 | A | 11/2000 | Brenneman et al. | 6,923,764 | B2 | 8/2005 | Aceti et al. |
| 6,162,639 | A | 12/2000 | Douglas | 6,936,476 | B1 | 8/2005 | Anderson et al. |
| 6,175,752 | B1 | 1/2001 | Say et al. | 6,988,996 | B2 | 1/2006 | Roe et al. |
| 6,176,865 | B1 | 1/2001 | Mauze et al. | 7,004,928 | B2 * | 2/2006 | Aceti et al. ................... 604/191 |
| 6,183,434 | B1 | 2/2001 | Eppstein | 7,025,774 | B2 | 4/2006 | Freeman et al. |
| 6,183,489 | B1 | 2/2001 | Douglas et al. | 7,052,652 | B2 | 5/2006 | Zanzucchi et al. |
| 6,187,210 | B1 | 2/2001 | Lebouiz et al. | 7,066,586 | B2 | 6/2006 | da Silva |
| 6,192,891 | B1 | 2/2001 | Gravel et al. | 7,066,890 | B1 | 6/2006 | Lam et al. |
| 6,200,296 | B1 | 3/2001 | Dibiasi et al. | 7,141,058 | B2 * | 11/2006 | Briggs et al. ................. 606/181 |
| 6,206,841 | B1 | 3/2001 | Cunningham et al. | 7,156,809 | B2 | 1/2007 | Quy |
| 6,214,626 | B1 | 4/2001 | Meller et al. | 7,192,061 | B2 | 3/2007 | Martin |
| 6,219,574 | B1 | 4/2001 | Cormier et al. | D540,343 | S | 4/2007 | Cummins et al. |
| 6,228,100 | B1 | 5/2001 | Schraga | 7,223,365 | B2 | 5/2007 | Freiherr Von Der Goltz |
| 6,230,051 | B1 | 5/2001 | Cormier et al. | 7,225,008 | B1 | 5/2007 | Ward et al. |
| 6,231,531 | B1 | 5/2001 | Lum et al. | 7,226,461 | B2 | 6/2007 | Boecker et al. |
| 6,241,862 | B1 | 6/2001 | McAleer et al. | 7,258,673 | B2 | 8/2007 | Racchini et al. |
| 6,242,207 | B1 | 6/2001 | Douglas et al. | D551,243 | S | 9/2007 | Young |
| 6,245,215 | B1 | 6/2001 | Douglas et al. | 7,270,970 | B2 | 9/2007 | Anderson et al. |
| 6,251,083 | B1 | 6/2001 | Yum et al. | 7,297,151 | B2 | 11/2007 | Boecker et al. |
| 6,251,260 | B1 | 6/2001 | Heller et al. | 7,343,188 | B2 | 3/2008 | Sohrab |
| 6,254,586 | B1 | 7/2001 | Mann et al. | 7,344,507 | B2 | 3/2008 | Briggs et al. |
| 6,255,061 | B1 | 7/2001 | Mori et al. | 7,427,377 | B2 | 9/2008 | Zanzucchi et al. |
| 6,256,533 | B1 | 7/2001 | Yuzhakov et al. | D599,373 | S | 9/2009 | Kobayashi et al. |
| 6,268,162 | B1 | 7/2001 | Phillips et al. | D601,578 | S | 10/2009 | Poulet et al. |
| 6,271,045 | B1 | 8/2001 | Douglas et al. | 7,803,123 | B2 | 9/2010 | Perez et al. |
| 6,272,364 | B1 | 8/2001 | Kurnik | 7,887,494 | B2 | 2/2011 | Emery et al. |
| 6,283,926 | B1 | 9/2001 | Cunningham et al. | D642,191 | S | 7/2011 | Barnett et al. |
| 6,289,230 | B1 | 9/2001 | Chaiken et al. | 8,012,103 | B2 | 9/2011 | Escutia et al. |
| 6,298,254 | B2 | 10/2001 | Tamada | 8,012,104 | B2 | 9/2011 | Escutia et al. |
| 6,299,578 | B1 | 10/2001 | Kurnik et al. | 2001/0001034 | A1 | 5/2001 | Douglas |
| 6,309,351 | B1 | 10/2001 | Kurnik et al. | 2001/0027328 | A1 | 10/2001 | Lum et al. |
| D450,711 | S | 11/2001 | Istvan et al. | 2001/0053891 | A1 | 12/2001 | Ackley |
| 6,312,612 | B1 | 11/2001 | Sherman et al. | 2002/0002326 | A1 | 1/2002 | Causey, III et al. |
| 6,312,888 | B1 | 11/2001 | Wong et al. | 2002/0002344 | A1 | 1/2002 | Douglas et al. |
| 6,322,808 | B1 | 11/2001 | Trautman et al. | 2002/0004640 | A1 | 1/2002 | Conn et al. |
| 6,329,161 | B1 | 12/2001 | Heller et al. | 2002/0006355 | A1 | 1/2002 | Whitson |
| 6,331,266 | B1 | 12/2001 | Powell et al. | 2002/0016568 | A1 | 2/2002 | Lebel et al. |
| 6,332,871 | B1 | 12/2001 | Douglas et al. | 2002/0020688 | A1 | 2/2002 | Sherman et al. |
| 6,334,856 | B1 | 1/2002 | Allen et al. | 2002/0023852 | A1 | 2/2002 | Mcivor et al. |
| 6,350,273 | B1 | 2/2002 | Minagawa et al. | 2002/0042594 | A1 | 4/2002 | Lum et al. |

| Publication No. | Date | Inventor |
|---|---|---|
| 2002/0052618 A1 | 5/2002 | Haar et al. |
| 2002/0087056 A1 | 7/2002 | Aceti et al. |
| 2002/0136667 A1 | 9/2002 | Subramanian et al. |
| 2002/0137998 A1 | 9/2002 | Smart et al. |
| 2002/0160520 A1 | 10/2002 | Orloff et al. |
| 2002/0169394 A1 | 11/2002 | Eppstein et al. |
| 2002/0169411 A1 | 11/2002 | Sherman et al. |
| 2002/0177761 A1 | 11/2002 | Orloff et al. |
| 2002/0183102 A1 | 12/2002 | Withers et al. |
| 2002/0188223 A1 | 12/2002 | Perez et al. |
| 2002/0198444 A1 | 12/2002 | Uchigaki et al. |
| 2003/0012693 A1 | 1/2003 | Otillar et al. |
| 2003/0028087 A1 | 2/2003 | Yuzhakov et al. |
| 2003/0028125 A1 | 2/2003 | Yuzhakov et al. |
| 2003/0039587 A1 | 2/2003 | Niermann |
| 2003/0083685 A1 | 5/2003 | Freeman et al. |
| 2003/0083686 A1 | 5/2003 | Freeman et al. |
| 2003/0116596 A1 | 6/2003 | Terasawa |
| 2003/0135166 A1 | 7/2003 | Gonnelli |
| 2003/0135333 A1 | 7/2003 | Aceti et al. |
| 2003/0153844 A1 | 8/2003 | Smith et al. |
| 2003/0153900 A1* | 8/2003 | Aceti et al. ................. 604/890.1 |
| 2003/0175987 A1 | 9/2003 | Verdonk et al. |
| 2003/0206302 A1 | 11/2003 | Pugh |
| 2003/0207441 A1 | 11/2003 | Eyster et al. |
| 2003/0208113 A1 | 11/2003 | Mault et al. |
| 2003/0211619 A1 | 11/2003 | Olson et al. |
| 2003/0212344 A1 | 11/2003 | Yuzhakov et al. |
| 2003/0212347 A1 | 11/2003 | Sohrab |
| 2004/0010207 A1 | 1/2004 | Flaherty et al. |
| 2004/0030353 A1 | 2/2004 | Schmelzeisen-Redeker et al. |
| 2004/0049219 A1 | 3/2004 | Briggs et al. |
| 2004/0059256 A1 | 3/2004 | Perez |
| 2004/0073140 A1 | 4/2004 | Douglas et al. |
| 2004/0092842 A1 | 5/2004 | Boecker et al. |
| 2004/0092995 A1 | 5/2004 | Boecker et al. |
| 2004/0096959 A1 | 5/2004 | Stiene et al. |
| 2004/0098009 A1 | 5/2004 | Boecker et al. |
| 2004/0102803 A1 | 5/2004 | Boecker et al. |
| 2004/0122339 A1 | 6/2004 | Roe |
| 2004/0132167 A1 | 7/2004 | Rule et al. |
| 2004/0138588 A1 | 7/2004 | Saikley et al. |
| 2004/0155084 A1* | 8/2004 | Brown .......................... 224/623 |
| 2004/0178218 A1 | 9/2004 | Schomakers et al. |
| 2004/0186394 A1 | 9/2004 | Roe et al. |
| 2004/0191119 A1 | 9/2004 | Zanzucchi et al. |
| 2004/0202576 A1 | 10/2004 | Aceti et al. |
| 2004/0236251 A1 | 11/2004 | Roe et al. |
| 2004/0238675 A1 | 12/2004 | Banaszkiewicz et al. |
| 2005/0010134 A1 | 1/2005 | Douglas et al. |
| 2005/0015020 A1 | 1/2005 | LeVaughn et al. |
| 2005/0096686 A1 | 5/2005 | Allen |
| 2005/0106713 A1 | 5/2005 | Phan et al. |
| 2005/0159678 A1 | 7/2005 | Taniike et al. |
| 2005/0187532 A1 | 8/2005 | Thurau et al. |
| 2005/0202567 A1 | 9/2005 | Zanzucchi et al. |
| 2005/0202733 A1 | 9/2005 | Yoshimura et al. |
| 2005/0215872 A1 | 9/2005 | Berner et al. |
| 2005/0215923 A1 | 9/2005 | Wiegel |
| 2005/0245844 A1 | 11/2005 | Mace et al. |
| 2005/0277972 A1 | 12/2005 | Wong et al. |
| 2006/0008389 A1 | 1/2006 | Sacherer et al. |
| 2006/0036134 A1 | 2/2006 | Tarassenko et al. |
| 2006/0117616 A1 | 6/2006 | Jones et al. |
| 2006/0135873 A1 | 6/2006 | Karo et al. |
| 2006/0155317 A1 | 7/2006 | List |
| 2006/0189908 A1 | 8/2006 | Kennedy |
| 2006/0204399 A1 | 9/2006 | Freeman et al. |
| 2006/0229533 A1 | 10/2006 | Hoenes et al. |
| 2006/0241517 A1 | 10/2006 | Fowler et al. |
| 2006/0257993 A1 | 11/2006 | McDevitt et al. |
| 2006/0259102 A1 | 11/2006 | Slatkine |
| 2006/0281187 A1 | 12/2006 | Emery et al. |
| 2007/0017824 A1 | 1/2007 | Rippeth et al. |
| 2007/0078313 A1 | 4/2007 | Emery et al. |
| 2007/0078358 A1 | 4/2007 | Escutia et al. |
| 2007/0083131 A1 | 4/2007 | Escutia et al. |
| 2007/0179404 A1 | 8/2007 | Escutia et al. |
| 2007/0179405 A1 | 8/2007 | Emery et al. |
| 2007/0255181 A1 | 11/2007 | Alvarez-Icaza et al. |
| 2007/0255302 A1 | 11/2007 | Koeppel et al. |
| 2008/0077048 A1 | 3/2008 | Escutia et al. |
| 2009/0156923 A1 | 6/2009 | Power et al. |
| 2010/0021948 A1 | 1/2010 | Lipman et al. |
| 2010/0185120 A1 | 7/2010 | Sacherer et al. |

FOREIGN PATENT DOCUMENTS

| | | |
|---|---|---|
| EP | 0 396 016 A2 | 11/1990 |
| EP | 0 396 016 A3 | 11/1990 |
| EP | 0 255 338 A2 | 2/1998 |
| EP | 1 266-607 A2 | 12/2002 |
| EP | 1 266-607 A3 | 12/2002 |
| EP | 1 360 934 A1 | 11/2003 |
| EP | 1 360 934 B1 | 11/2003 |
| EP | 1 486 766 A1 | 12/2004 |
| EP | 1 486 766 B1 | 12/2004 |
| EP | 1 529-489 A1 | 5/2005 |
| EP | 1 529-489 B1 | 5/2005 |
| EP | 1 769 735 A1 | 4/2007 |
| JP | 63-305841 A | 12/1988 |
| JP | 3-63570 A | 3/1991 |
| JP | 03093189 | 4/1991 |
| JP | 7-67861 A | 3/1995 |
| JP | 7-213925 | 8/1995 |
| JP | 9-168530 A | 6/1997 |
| JP | 9-313465 A | 9/1997 |
| JP | 9-266889 A | 10/1997 |
| JP | 9-294737 A | 11/1997 |
| JP | 10 024028 A | 1/1998 |
| JP | 10-318970 | 12/1998 |
| JP | 2000126161 A | 5/2000 |
| JP | 2000-254111 A | 9/2000 |
| JP | 2001-159618 A | 6/2001 |
| JP | 2001-515203 A | 9/2001 |
| JP | 2001-305096 A | 10/2001 |
| JP | 2001-330581 A | 11/2001 |
| JP | 2002-502045 A | 1/2002 |
| JP | 2004-000598 | 1/2004 |
| JP | 2004-522500 A | 7/2004 |
| JP | 2005-503538 | 2/2005 |
| JP | 2005-087613 A | 4/2005 |
| JP | 2005-237938 A | 9/2005 |
| JP | 2005-527254 A | 9/2005 |
| JP | 2006-512969 A | 4/2006 |
| JP | 2006-512974 A | 4/2006 |
| JP | 2006-516723 A | 7/2006 |
| JP | 2006-521555 A | 9/2006 |
| JP | 2006-527013 A | 11/2006 |
| JP | 2007-521031 A | 8/2007 |
| WO | WO-94/13203 A1 | 6/1994 |
| WO | WO-95/10223 A2 | 4/1995 |
| WO | WO-95/10223 A3 | 4/1995 |
| WO | WO-96/04857 A1 | 2/1996 |
| WO | WO-96/14026 A1 | 5/1996 |
| WO | WO-96/25088 A1 | 8/1996 |
| WO | WO-97/15227 A1 | 5/1997 |
| WO | WO-97/29847 A1 | 8/1997 |
| WO | WO-97/30344 A1 | 8/1997 |
| WO | WO-97/41421 A1 | 11/1997 |
| WO | WO-98/31275 A1 | 7/1998 |
| WO | WO-98/35225 A1 | 8/1998 |
| WO | WO-99/12008 A1 | 3/1999 |
| WO | 99/44508 A | 9/1999 |
| WO | WO-00/09184 A1 | 2/2000 |
| WO | WO-00/13573 A1 | 3/2000 |
| WO | WO-00/14269 A1 | 3/2000 |
| WO | WO-00/14535 A1 | 3/2000 |
| WO | WO-00/18449 A2 | 4/2000 |
| WO | WO-00/18449 A3 | 4/2000 |
| WO | WO-00/36400 A1 | 6/2000 |
| WO | WO-00/42422 A1 | 7/2000 |
| WO | WO-00/74763 A2 | 12/2000 |
| WO | WO-00/74763 A3 | 12/2000 |
| WO | WO-00/78208 A1 | 12/2000 |
| WO | WO-01/16575 A1 | 3/2001 |
| WO | WO-01/52727 A1 | 7/2001 |
| WO | 01/64105 A1 | 9/2001 |
| WO | WO-01/72220 A1 | 10/2001 |

| | | |
|---|---|---|
| WO | WO-01/80728 A1 | 11/2001 |
| WO | WO-01/85233 A2 | 11/2001 |
| WO | WO-01/85233 A3 | 11/2001 |
| WO | WO-01/91634 A2 | 12/2001 |
| WO | WO-01/91634 A3 | 12/2001 |
| WO | 02/00101 A2 | 1/2002 |
| WO | 02/49507 A1 | 6/2002 |
| WO | WO-02/49509 A2 | 6/2002 |
| WO | WO-02/49509 A3 | 6/2002 |
| WO | WO-02/082052 A2 | 10/2002 |
| WO | WO-02/082052 A3 | 10/2002 |
| WO | WO-02/093144 A1 | 11/2002 |
| WO | WO-02/100251 A2 | 12/2002 |
| WO | WO-02/100251 A3 | 12/2002 |
| WO | WO-02/101359 A2 | 12/2002 |
| WO | WO-02/101359 A3 | 12/2002 |
| WO | WO-03/030984 A1 | 4/2003 |
| WO | WO 03/071940 A1 | 9/2003 |
| WO | WO-2004/062499 A1 | 7/2004 |
| WO | WO-2004/062500 A1 | 7/2004 |
| WO | WO-2004-062500 C1 | 7/2004 |
| WO | WO-2004/064636 A1 | 8/2004 |
| WO | WO-2005/006939 A2 | 1/2005 |
| WO | WO-2005/006939 A3 | 1/2005 |
| WO | WO-2005/009238 A1 | 2/2005 |
| WO | WO-2005-084543 A3 | 9/2005 |
| WO | WO-2005/084546 A2 | 9/2005 |
| WO | WO-2005/085995 A1 | 9/2005 |

* cited by examiner

FULLY INTEGRATED WEARABLE OR HANDHELD MONITOR

FIELD

The present invention relates to devices, arrangements and methods involving body fluid sampling and/or analysis. In certain embodiments, the present invention is directed to integrated monitoring and body fluid sampling devices and methods that are wearable, handheld, or easily converted for use in either manner.

BACKGROUND

In the discussion that follows, reference is made to certain structures and/or methods. However, the following references should not be construed as an admission that these structures and/or methods constitute prior art. Applicants expressly reserve the right to demonstrate that such structures and/or methods do not qualify as prior art.

According to the American Diabetes Association, diabetes is the fifth-deadliest disease in the United States and kills more than 213,000 people a year, the total economic cost of diabetes in 2002 was estimated at over $132 billion dollars. One out of every 10 health care dollars is spent on diabetes and its complications. The risk of developing type I juvenile diabetes is higher than virtually all other chronic childhood diseases. Since 1987 the death rate due to diabetes has increased by 45 percent, while the death rates due to heart disease, stroke, and cancer have declined.

A critical component in managing diabetes is frequent blood glucose monitoring. Currently, a number of systems exist for self-monitoring by the patient. Most fluid analysis systems, such as systems for analyzing a sample of blood for glucose content, comprise multiple separate components such as separate lancing, transport, and quantification portions. These systems are bulky, and often complicated and confusing for the user. These systems require significant user intervention. Current systems are not discreet, which, under certain social circumstances, may result in diabetics not monitoring their glucose levels.

Attempts have been made in the past to take steps toward automation of the testing process. Specifically, the Sof-Tact® System offered by Medisense in the early 2000s had the capability to test automatically at alternate sites without any user intervention, but only after each lancet and test strip had been manually loaded into the device. The device is configured for handheld operation only and is rather large. This meter is no longer available on the market.

A device similar to the Soft-Tact® device is disclosed in U.S. Patent Application Publication No. 2004/0138588 A1. This device attempts to integrate all the functions required to complete a glucose test into one device. This device however still requires the user to load a lancet and a test strip prior to each individual testing event. This device is also configured for handheld operation only.

This device is described in U.S. Patent Application Publication No. 2005/0010134 A1, and U.S. Pat. No. 6,793,633 B2 uses a spring, or motor driven mechanism to apply pressure around the target wound area. However, the device therein is not a fully integrated system. From the description it appears that the user must insert a new lancet and test strip assembly for each test. Another disadvantage of the device is configured only for handheld operation.

In summary, most current systems that are not integrated and thus involve many pieces that are not convenient and make the test difficult to perform discreetly. Other current devices that may be somewhat integrated but still require significant user intervention, are not discreet, and require more than one device to complete the test.

SUMMARY

According to the present invention, there are provided body fluid sampling and monitoring devices and methods that may address one or more of the shortcomings noted above associated with conventional systems and devices. According to the present invention, there may also be provided improved monitoring and body fluid sampling devices and methods that permit handheld operation, wearable operation, and/or convertible for use in either manner.

One optional advantage of the invention over current devices is that it can be fully integrated and automated. The device can be packaged and designed such that it may be hand held or wearable, perhaps in the form of a wristwatch, and requires minimal or no intervention from the wearer in order to carry out testing, thus enhancing discreet testing. The invention also optionally enables an array of tests to be performed through use of a disposable cartridge or unit. For example, this system allows the user to load one cartridge that contains everything necessary for multiple tests. Another possible advantage of the invention is that it requires less body fluid for an accurate test than other systems currently available. This also facilitates reduction of pain experienced by the user during testing. The integrated nature of a device of the invention may also facilitate accurate tracking of blood glucose levels over time. Current systems rely on the user to test at specific intervals; a device constructed according to the principles of the present invention can be capable of testing independent of user input. A device of the present invention may optionally be constructed to give the user the option of automated/scheduled testing and/or on-demand testing.

It is to be understood that reference herein to first, second, third and fourth components (etc.) does not limit the present invention to embodiments where each of these components is physically separable from one another. For example, a single physical element of the invention may perform the features of more than one of the claimed first, second, third or fourth components. Conversely, a plurality of separate physical elements working together may perform the claimed features of one of the claimed first, second, third or fourth components. Similarly, reference to first, second (etc.) method steps does not limit the invention to only separate steps. According to the invention, a single method step may satisfy multiple steps described herein. Conversely, a plurality of method steps could, in combination, constitute a single method step recited herein.

According to another optional aspect of the present invention, there is provided an integrated body fluid sampling and analysis device, the device comprising a housing, the housing containing a plurality of body fluid sampling and analysis sites, each of the sites comprising a skin-penetration member, a body attachment element, and a quick release mechanism connecting the housing and the body attachment element.

According to a further optional aspect, the present invention provides an arrangement comprising a housing containing one or more components configured for at least one of body fluid sampling or analysis, and a body attachment element, wherein the housing and the body attachment element are connected by a quick-release mechanism configured to facilitate removal of the housing from the body attachment element.

According to yet another optional aspect, the present invention provides a method of performing at least one of body fluid sampling or analysis, the method comprising providing a housing with one or more components configured for at least one of body fluid sampling or analysis, the components comprising at least one skin-piercing member, providing a body attachment element, connecting the housing to the body attachment element in a releasable manner, removing the housing from the body attachment element, applying the housing to a surface of the skin, and piercing the skin with the at least one skin-penetration members.

As used herein "digital" means fingers or toes. "Digital body fluid" means expression of body fluid a wound created on the fingers or toes, and encompasses lancing sites on the dorsal or palm side of the distal finger tips.

As used herein "alternate-site" means a location on the body other than the digits, for example, the palm, forearm or thigh. "Alternate-site body fluid sampling" means expression of body fluid from the lancing site on a surface of the body other than the fingers or toes, and encompasses lancing sites on the palm, forearm, and thigh.

As used herein, "body fluid" encompasses whole blood, intestinal fluid, and mixtures thereof.

As used herein "integrated device" or "integrated meter" means a device or meter that includes all components necessary to perform sampling of body fluid, transport of body fluid, quantification of an analyte, and display of the amount of analyte contained in the sample of body fluid.

BRIEF DESCRIPTION OF THE DRAWING FIGURES

The following description of preferred embodiments can be read in connection with the accompanying drawings in which like numerals designate like elements and in which.

DETAILED DESCRIPTION

Figure 1A:
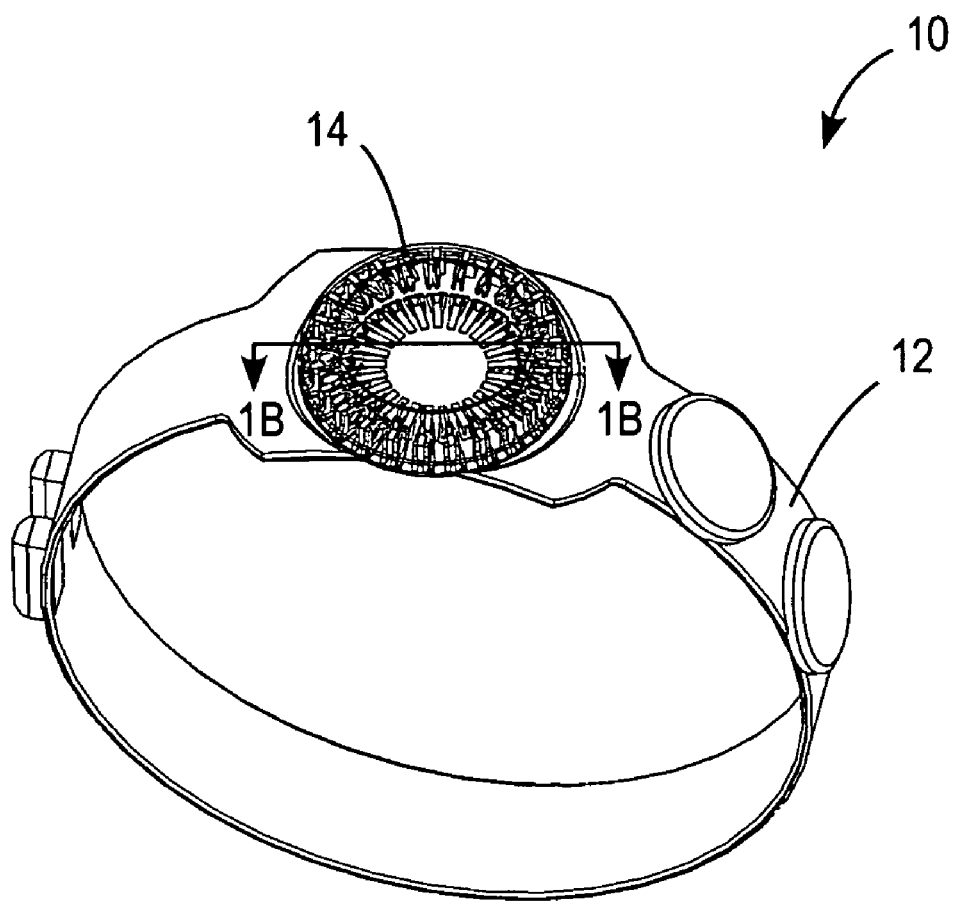
FIG. 1A is a perspective view of an integrated device constructed according to the present invention.

Exemplary arrangements and methods for the detection and measurement of the presence and/or concentration of a target analyte, such as glucose, bilirubin, alcohol, controlled substances, toxins, hormones, proteins, etc., will now be described.

According to certain embodiments, the current device is a fully integrated, electromechanical system or device used in the sampling and/or analysis of a bodily fluid. One possible body fluid is whole blood and one possible analyte is glucose. The fully integrated device of the present invention is much smaller than any current commercially available semi-integrated, or multi-piece glucose testing system, using blood as the analyte. The fully integrated nature of the invention reduces the total number of parts a user must carry to complete a test from about a minimum of 3-8 (lancet, lancer, test strip, calibration fluid, alcohol wipe, carrying case, etc.) to 1-2 pieces (integrated device, optional carrying case). A fully integrated device formed according to the present invention requires little or no user intervention to carry out testing. For example, the device may automatically perform testing at predetermined intervals. Alternatively, the integrated device can offer automatic single button operation that significantly reduces the level of dexterity required for operation compared with currently available systems. The device of the present invention may comprise a reusable unit and a disposable unit comprising a plurality of test subsystems. The device or system may be wearable or may be hand held. The reusable portion of the device may include a housing, an attachment mechanism, and a user interface display. It may include an energy storage system, mechanisms to facilitate the testing process including motors, vacuum pumps, and mechanical stored energy systems. The reusable unit or portion may also include microprocessors, and other electronics in support of analyte quantification. The reusable portion may also include optical systems for analyte quantification. The reusable unit may include mechanisms for indexing between multiple test sites, and may also include user interface devices such as buttons, knobs, and microphones. The device or system of the present invention may also include a disposable portion. The disposable portion may include an array of skin piercing elements attached to guides, triggers and/or actuation mechanisms. The disposable portion may also include mechanisms for transporting a sample of body fluid from the skin surface into other areas of the device. According to certain embodiments, at least a portion of the transport operation is integrated into the skin-piercing element. The disposable portion may also include analyte quantification members that may be separate from or integrated with the transport member. The analyte quantification members may be designed to optically or electrochemically indicate detectable signals when exposed to the analyte of interest.

The disposable portion may also include a skin-interfacing member, possibly a soft silicone footprint. The skin interfacing member can optionally be constructed of any material that facilitates sample acquisition via conditioning the skin prior to, during and/or after piercing. The skin interface may be included in the reusable portion of the device.

The disposable portion may include an energy source. The disposable portion may also include a housing designed to enclose, and/or seal the analyte quantification members. The disposable portion may also include mechanisms, or be designed to allow for user-adjustable skin piercing depth. The disposable portion may also include vacuum chambers as well as a means to provide an airtight seal against the skin.

An integrated device or meter of the type described above is illustrated in FIGS. 1A-1C. As illustrated therein the integrated device 10 is discreet, portable, and wearable, and may generally be in the form of a wristwatch. The device 10 includes an attachment element or band configured to secure the device to the body or wrist of the user. The device 10 further comprises a housing 14 that contains one or more of the components used for sampling and/or analysis, as described above. The device 10 may further comprise a disposable portion and a reusable portion, as further described above.

According to the present invention, it is possible, but not mandatory, to form the integrated device with a low height profile to make the device as compact and discreet as possible. Thus, according to the present invention, the actuator can be designed to accelerate the skin-piercing element along a curved or rotational path. This construction provides for a more compact height profile of the device. Any suitable mechanism for accelerating the needle along a curved or rotational path is contemplated. One such mechanism is a torsional spring element. The integrated device or meter 10 also includes a housing 16 formed of any suitable material. One or more actuation posts, or triggers, 18 are fixably mounted to a base plate 20 such that each one individually constrains a spring actuator 22 in a cocked position such that the spring is in such a state that it stores elastic energy. Skin piercing elements 24, which may be in the form of lancets or hollow needles, are mounted over the one or more actuation posts 18. Upon release of a trigger element 18 the skin piercing element 24 is driven into the skin of the user or wearer. The trigger may be released by one of a variety of different physical means. The trigger may be a bimetallic strip that, when heated, deforms enough so that the spring retainer clears the trigger and is released. The trigger may alternatively be a fuse such that when current is passed through it, it breaks causing the actuator to be released. The device or arrangement 10 may be constructed such that each individual skin-piercing element 24 is provided with its own actuator 22. Optionally, the actuator 22 may be provided in the form of a torsional spring, as illustrated.

Figure 1B:
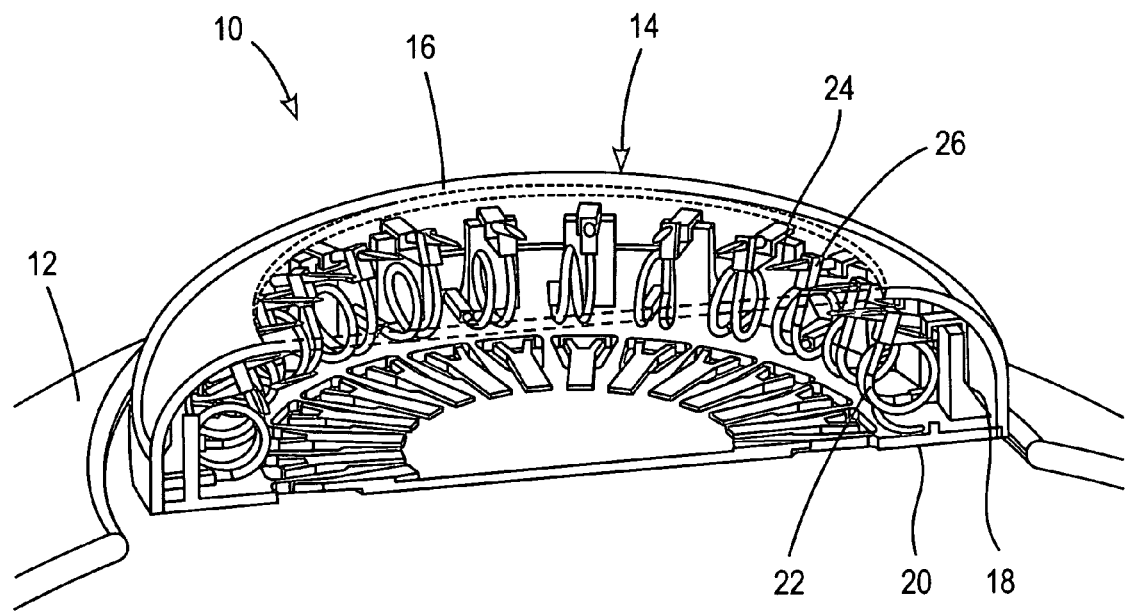
FIG. 1B is a sectional view taken along line 1B-1B of FIG. 1A.
Figure 1C:
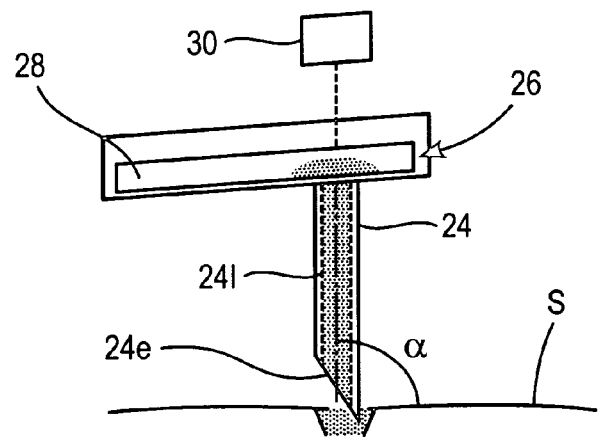
FIG. 1C is a schematic illustration of an arrangement formed according to one aspect of the present invention.

The actuator spring elements 22 may be provided to the user in a pre-cocked position, as illustrated in FIG. 1B. The acceleration path of the skin-piercing element or needle 24 may begin up to 180 degrees from the angle of impact with the skin S of the user. According to one beneficial aspect, the pivot point of the actuator or torsional spring elements is provided as close as possible to the plane lying on the surface of the skin S in order to ensure that the skin piercing element 24 strikes the skin S at an angle $\alpha$ which is as close to 90 degrees as possible. The torsional spring elements 22 act as a guide for the skin-piercing element or needle 24 to that locates the end 24e in the body fluid sample after actuation so as to draw the body fluid into the lumen 24l of the needle. In this regard, the actuator or torsional spring elements 22 may be designed such that its neutral position will locate the end 24e of the skin-piercing element 24 in the opening created by the skin piercing operation at, above, or below the surface of the skin S. Preferably, the torsional spring elements may be designed such that a small spring bias urges the skin-piercing element or needle 24 into the opening at or below the surface of the skin S.

Another advantage of this aspect of the present invention is that the actuator torsional spring elements 22 do not require a positive stop to limit the penetration depth of the skin-piercing element 24. It has been observed that elimination of a hard stop may provide certain beneficial effects. Namely, it has been observed that devices that include a hard stop experience a shock and resulting vibration and/or stirring action when the stop is impacted. It is theorized that this motion may increase the observable wound and/or the perceived pain associated with sampling. According to this embodiment, the depth of penetration of the skin-penetrating member 24 is determined by a number of factors, including the design of the sharp, the actuation force and the skin's resistance to penetration at the chosen sampling site, and the height that the skin is raised up (if any) by application of a vacuum catalyst.

When the skin piercing element 24 is in the form of a needle having an inner passageway or lumen 24l, an analyte quantification member 26 that may comprise an assay pad 28 is provided in communication with the lumen 24l of the needle such that the quantification member can receive a sample of blood produced by the piercing of the user's skin with the needle. The quantification member 26 can be in optical communication with a detector array 30 that reads a color change on the assay pad or can be an electrochemical means according to an alternative embodiment.

Figure 2:
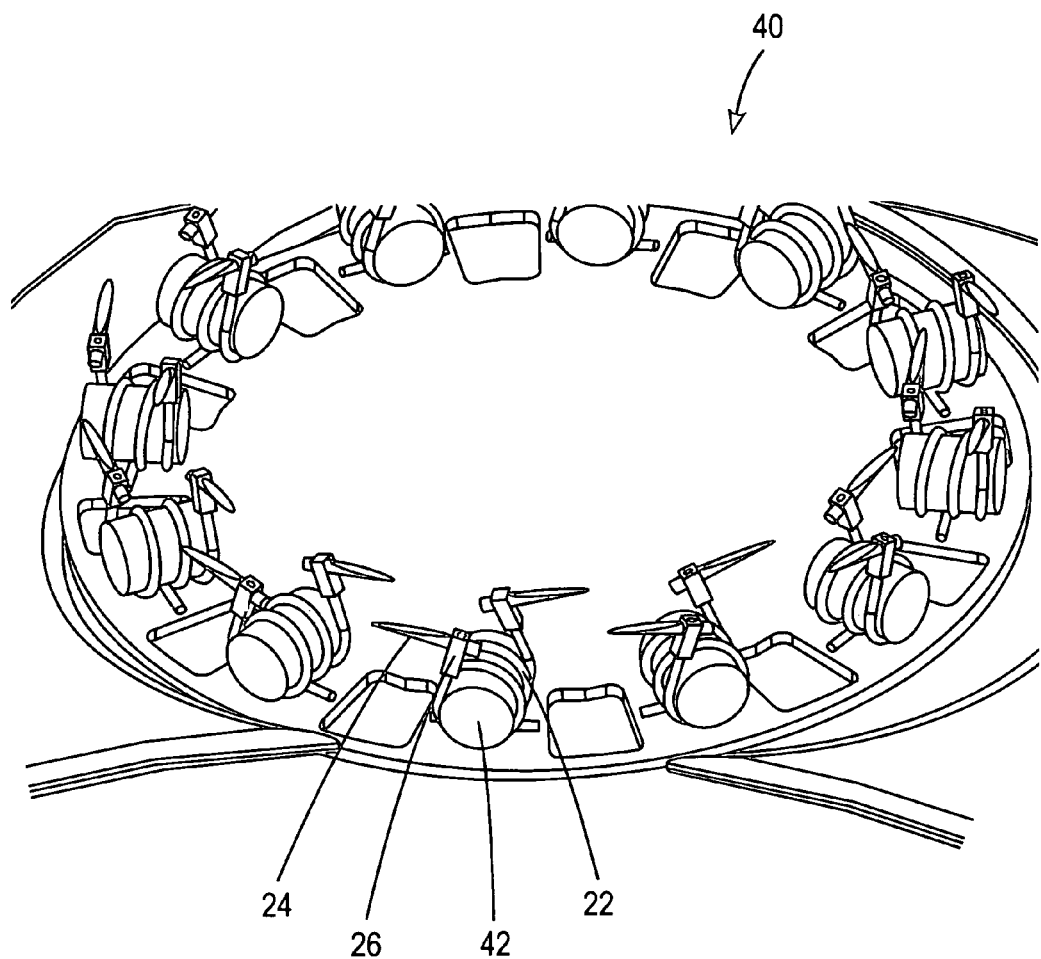
FIG. 2 is a perspective view of an arrangement constructed according to an alternative embodiment of the invention.

One possible modification of the arrangement 10 is illustrated in FIG. 2. As illustrated therein, an arrangement 40 is similar to the previously described arrangement 10, except that the skin piercing elements or needles 24 are oriented in a circumferential manner, as opposed to the generally radial orientation of the arrangement 10. As illustrated therein, the actuators or torsional spring elements 22 are mounted to triggering members 42 that, according to the illustrated embodiment are in the form of a rotary post or spindle. This arrangement can work with a variety of triggers. In the current embodiment, each spring has a trigger that trips the cocked spring thus releasing the leg holding the needle and causing the needle to accelerate. The triggering members 42 may comprise a rotational actuator such as a piezoelectric motor similar to the MiniSwis miniature piezo motors (e.g., model 6 TRAPEZ 4 V1). This motor can rotate an arm to trip a lever that holds the spring in the cocked position. Furthermore, according to certain alternative embodiments, the rotational piezo-motor may advance in the opposite rotational direction to catch the spring in order to dwell the skin-piercing elements or needle in the body fluid sample so that the body fluid may travel up into the lumen 24l via capillary action.

Figure 3:
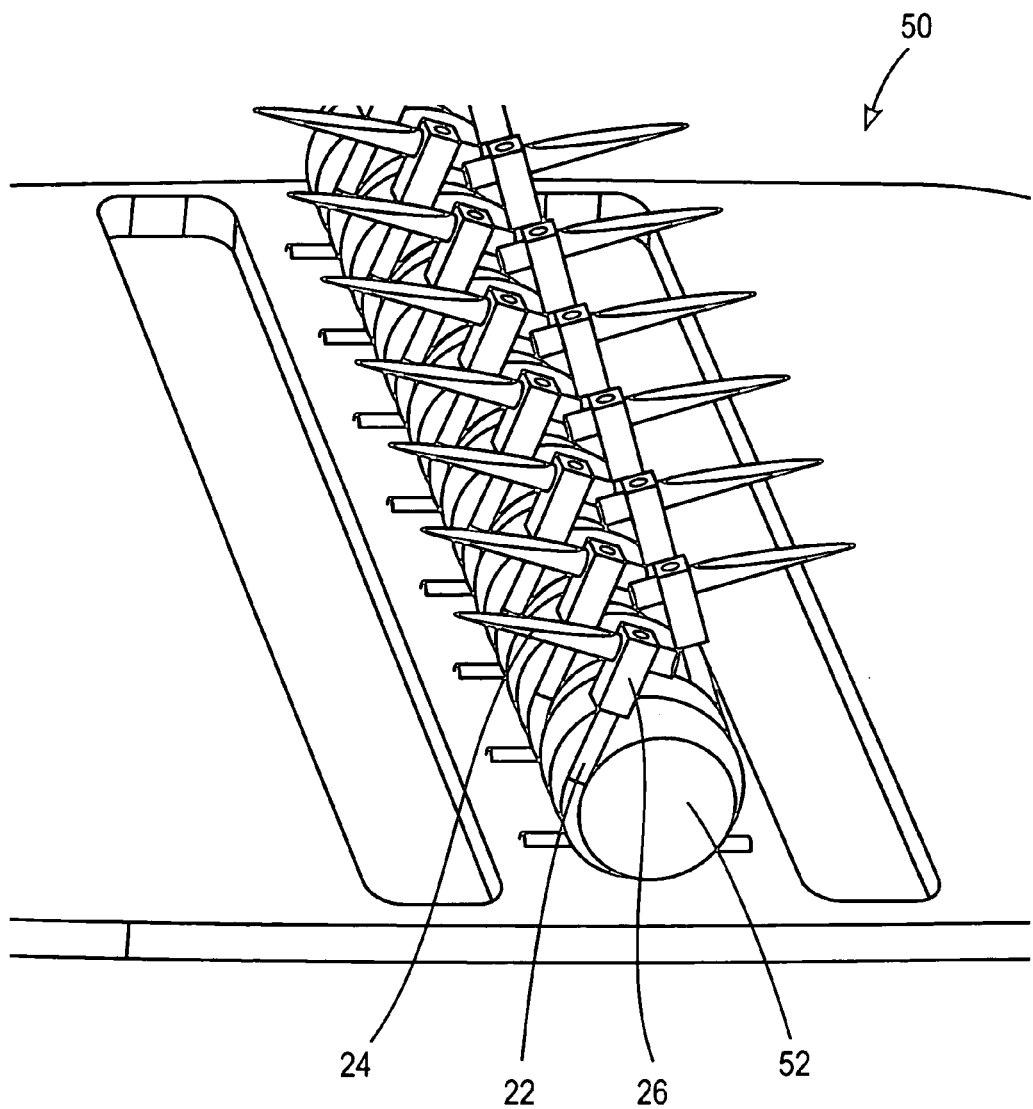
FIG. 3 is a perspective view showing an arrangement according to a further embodiment.

Another possible modification of the arrangement 10 is illustrated in FIG. 3. As illustrated therein, an arrangement 50 is similar to the previously described arrangements (10, 40), except that the skin piercing elements or needles 24 are oriented in a linear manner, as opposed to the generally radial orientation of the arrangement 10, or circumferential manner of the arrangement 40. As illustrated therein, the actuators or torsional spring elements 22 are mounted to pivot member(s)

52. This arrangement accommodates a variety of different trigger mechanisms such as fusible links, bimetallic strips, rotating cams, etc.

Figure 5:
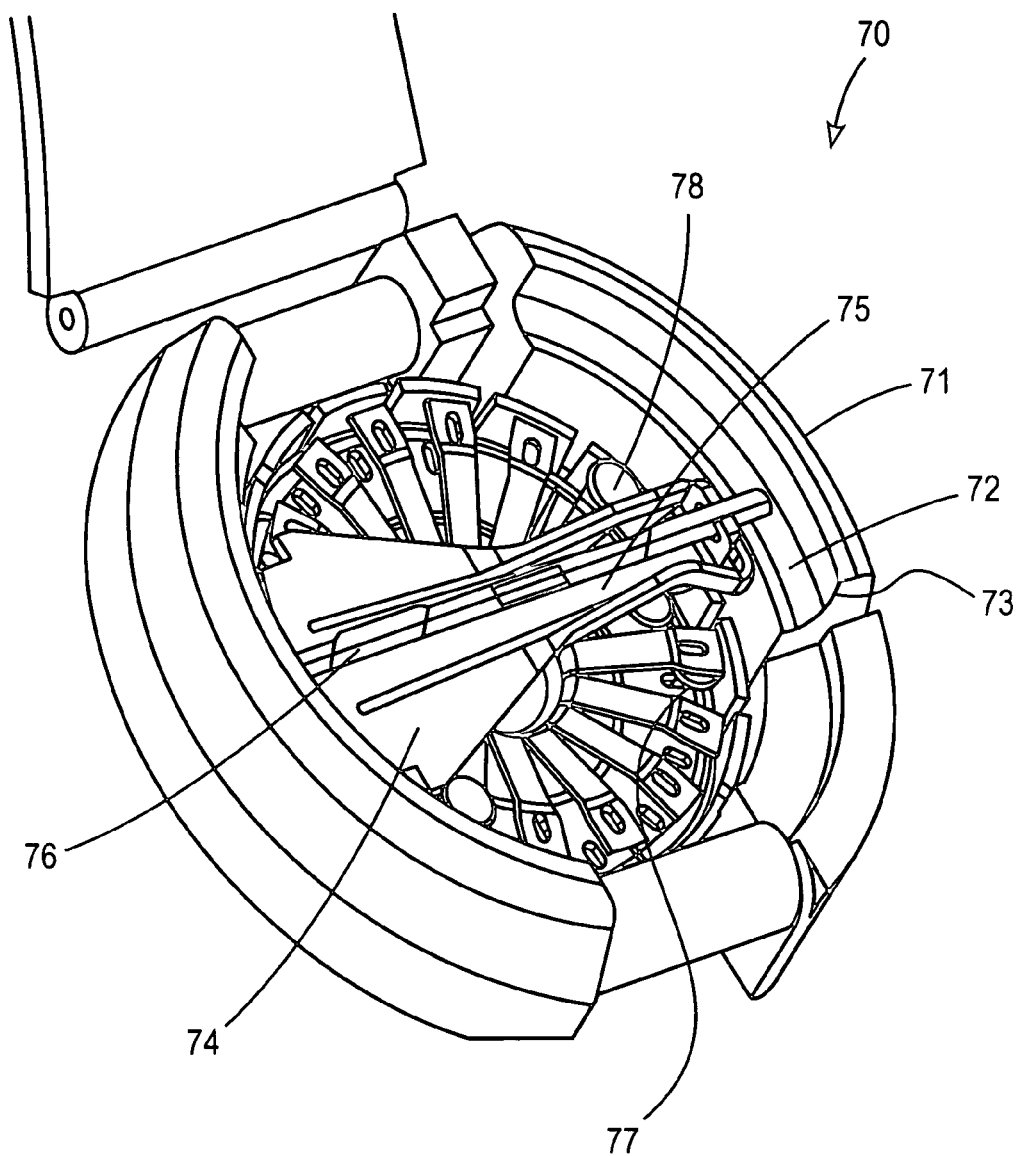
FIG. 5 is a perspective view of yet another alternative arrangement of the present invention.

According to certain embodiments of the present invention, a single actuator mechanism (e.g., a motor) can index to drive one or more selected skin piercing members that form part of an array into the skin (see, e.g., FIG. 5). Other alternative embodiments include one actuator per skin piercing member (see, e.g., FIG. 1B).

According to alternative embodiments of the present invention, certain actuators that are contemplated can cause the driven skin-piercing element (or needle) to rapidly oscillate, re-enter or repeatedly penetrate the skin at the sampling site. The number of penetrations per actuation or sampling event can vary between 2-20 times. The frequency of oscillation of the skin-piercing element may vary and can be on the order of 200-600 Hz. It has been observed that such oscillation does not appear to produce an increase in the observable wound or perceived pain by the user. The skin-piercing element may be driven at any suitable speed.

The invention described herein suggests that the skin-piercing member can be driven into the skin by some controlled force. There are several embodiments of actuators that can perform this function including torsional springs, compression springs, cantilever beams, linear voice coils/solenoids, pneumatic cylinders, as well as others. A torsional spring embodiment has been described above. Additional, exemplary embodiments of such actuators are illustrated in FIGS. 4-7.

Figure 4:
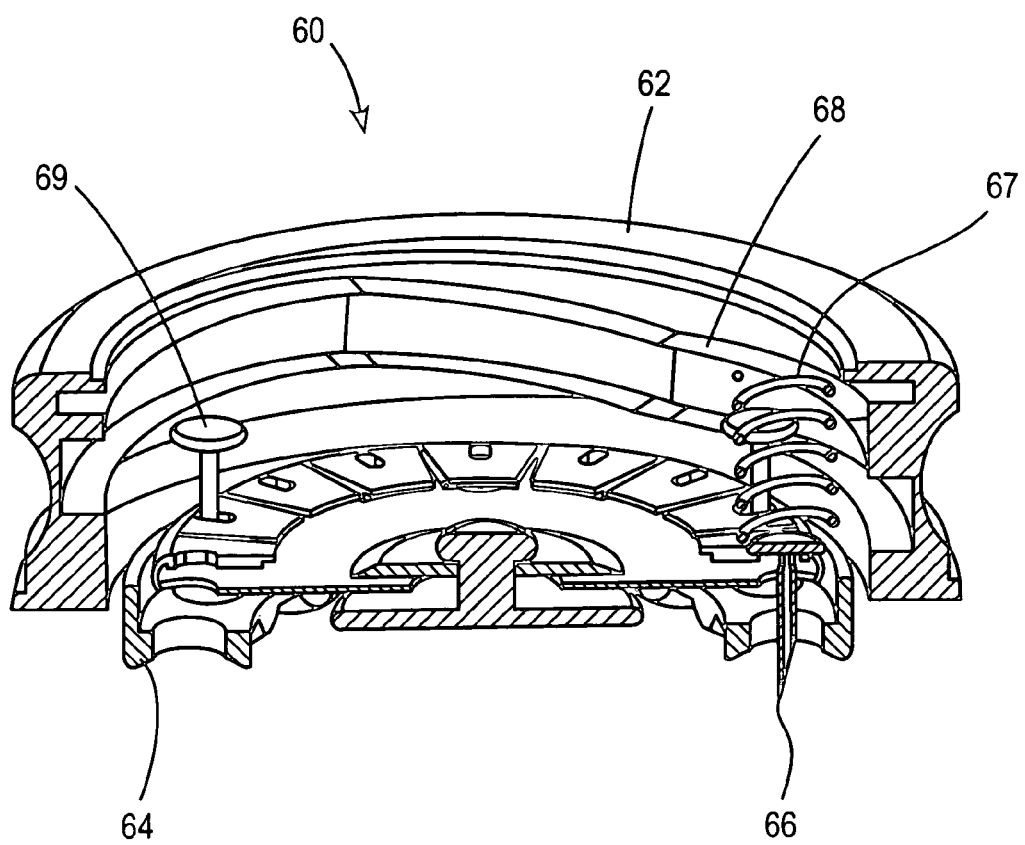
FIG. 4 is a cut-away view of a further alternative arrangement of the present invention.

FIG. 4 illustrates a device or arrangement 60 formed according to the principles of the present invention. As illustrated in FIG. 4, the device or arrangement 60 includes a housing member 62. The housing member 62 can be constructed of any suitable material, such as a polymer or metal. The housing 62 is preferably constructed such that it forms part of a discrete wearable or hand held device. The device may generally be in the form of a wristwatch. Within the housing 62 there is disposed a relatively rotatable camming or ramping surface 64. The device or arrangement 60 further includes a guide element or plate 64. A skin-piercing element 66, such as a hollow needle, is disposed such that it may travel through the guide element or plate 64. An actuator 67, such as the illustrated coil spring, is also disposed within the housing 62. The actuator or coil spring 67 interacts with the relatively movable camming or ramping surface 68 such that the energy stored in the actuator or coil spring 67 is released when a predetermined release point formed along the rotating camming or ramping surface 68 is reached. This released stored energy is then transferred to the skin-piercing element 66 such that it is driven into the skin of the user or wearer of the device. As further illustrated in FIG. 4, the skin piercing element 66 may be provided with an analyte quantification member 69, of the type previously described. The quantification member 69 may include suitable quantification media for analysis of the body fluid sample received therein. Such media may include one or more chemical reagents that react with an analyte present in the sample, thereby producing a detectable signal, as discussed herein. Alternatively, an electrochemical media may be utilized, such electrochemical media per se being well known in the art.

An additional alternative embodiment is illustrated in FIG. 5. The device or arrangement 70 illustrated in FIG. 5 includes a housing member 71 also formed of any suitable material, such as those described above, and of which also may form part of an overall wearable and discrete device. A movable or rotatable surface 72 is provided within the housing 71. A break 73 is formed along this relatively movable or rotatable surface 72. An indexing element 74 is mounted within the housing. A release member 75 may be disposed on the indexing member 74. As the actuation release member 75 comes into registry with the break 73 and the relatively movable or rotatable surface 72, the stored energy contained in an actuator or spring member 76 can then be released, driving a skin piercing element 77 into the surface of the skin of the user or wearer. According to the illustrated embodiment, the skin-piercing element 77 is in fluid communication with an analyte quantification member 78 of the type previously described. Further, the spring member 76 can be formed as a cantilevered spring arm that provides the stored spring energy which, when released as the described above, drives the skin piercing element 77 into the surface of the skin. As evidenced from FIG. 5, the device or arrangement 70 includes a single actuator that is movable, and indexes with individual skin-piercing elements.

Figure 6:
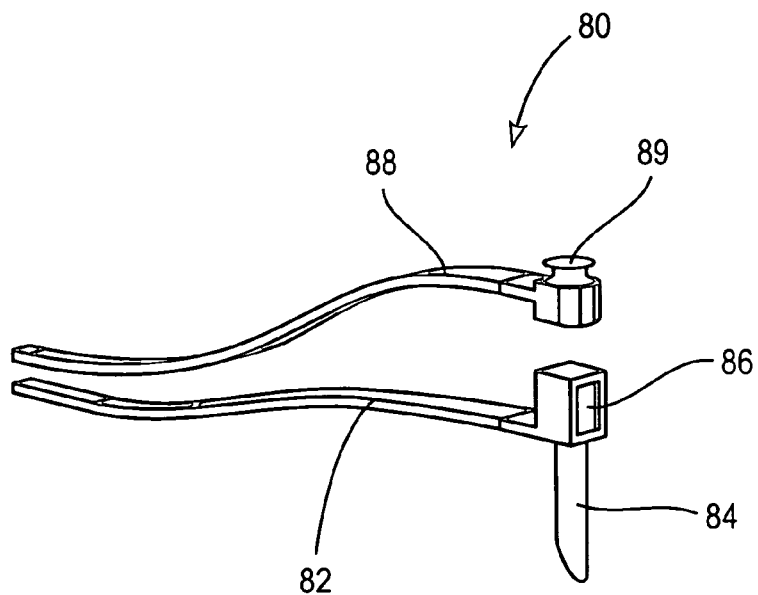
FIG. 6 is a perspective view of an actuation arrangement constructed according to a further alternative embodiment of the present invention.

A further alternative embodiment of the present invention is illustrated in FIG. 6. The arrangement 80 of FIG. 6 includes a first arm 82 upon which is mounted a skin-piercing element 84, such as a hollow needle or a lancet. In the illustrated embodiment, skin-piercing element 84 is a hollow needle. The skin-piercing element 84 may be provided in fluid communication with an analyte quantification member 86 of the type previously described. A second mounting arm 88 is disposed above the first arm 82, as illustrated. Attached to the end of the mounting arm 88 is a weight 89, which can be driven into the skin piercing element 84, thereby driving the skin-piercing element 84 into the surface of the skin of the user or wearer. Varying the mass of weight 89 attached to the mounting arm 88 and/or the vertical displacement of the weight relative to the first arm can control the magnitude of the driving force behind the skin-piercing element 84. It should be understood that constructions where each skin-piercing element 84/quantification member 86 combination may have their own individual second mounting arm 88/weight 89 associated therewith, and constructions where a single second arm 88/weight 89 is moveable to index with each skin-piercing element 84/quantification member 86 combination are both contemplated by the present invention.

The driving element may be another type of actuator besides a beam such as, a coil spring, solenoid, voice coil, or any other type of mechanism that can accelerate to enough momentum to impact or push the skin-piercing element such that it penetrates the skin to the proper depth.

Figure 7:
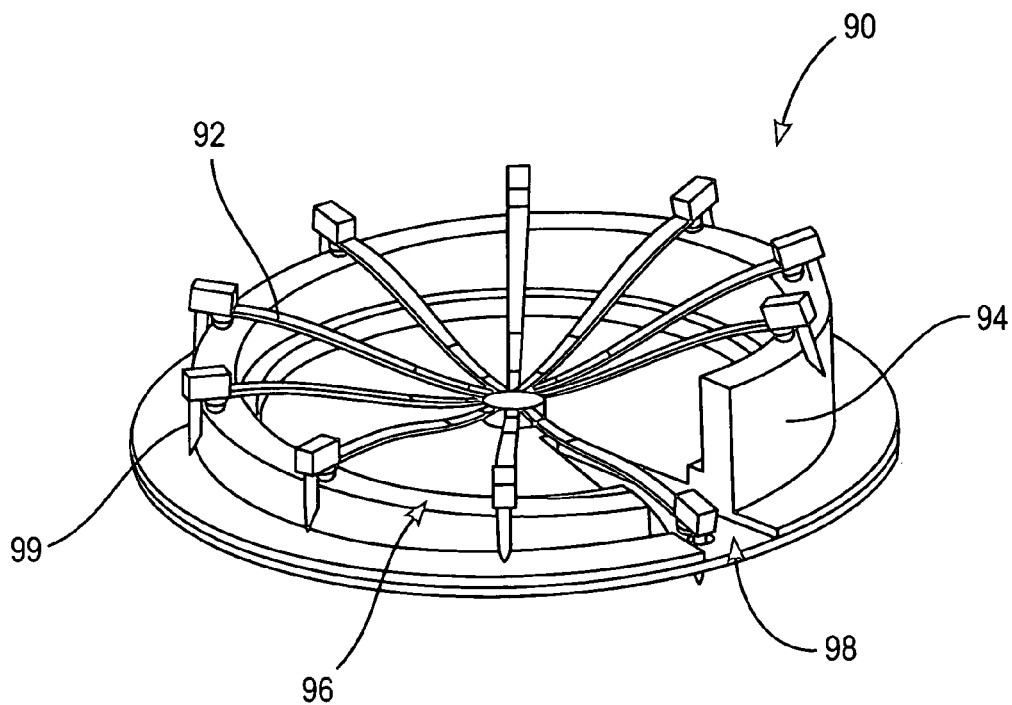
FIG. 7 is a perspective view of an actuation arrangement formed according to yet another alternative embodiment of the present invention.

An additional illustrative embodiment is depicted in FIG. 7. This embodiment includes an arrangement 90 that uses a cantilever beam 92 actuator triggered via a cam/ramp system 94. In this system a motor or spring (not shown) rotates a cam 94 that has a specifically designed ramp path 96. As the cam 94 rotates the beam 92 rides up the cam 94, once the beam 92 has been lifted to the desired height the beam comes into communication with a break 98 in the ramp path 96 and beam 92 is released. In one embodiment the device is laid out such that after one beam is triggered the cam 94 continues to rotate and the next beam 92 is lifted and released. This pattern continues until after complete revolution all of the sites have been fired. In another embodiment each revolution of the cam 94 lifts and releases a single cantilevered beam 92. This single beam 92 is indexed to drive every skin-piercing element 99 into the skin.

Another alternative embodiment uses small stepper motors that rotate to release a latch. Specifically a small stepper motor is attached to a rotating or flexible "arm" feature, as that arm rotates it contacts a latch, knocks it off of its rest point and releases the spring.

Yet another embodiment uses a nitinol switch that changes shape when current is applied to it. As the shape of the trigger changes the actuator is released. According to a further embodiment, a breakable wire switch works on the concept that some materials weaken when exposed to heat or current. A small section of this material would be used to hold the actuator in the cocked position. To release the actuator, a current is passed through the wire. Similarly, heat can be applied to a thread-like material or other material to sever the material by melting or burning.

Figure 8A:
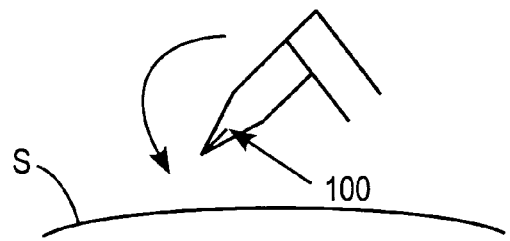
FIGS. 8A-8D are schematic illustrations of four alternative skin-penetrations members formed according to certain embodiments of the present invention.
Figure 8B:
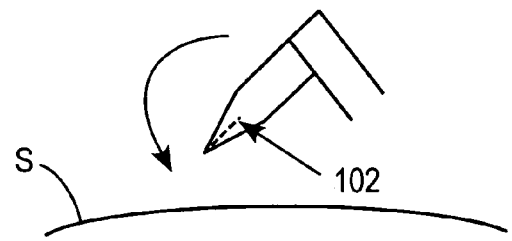
Figure 8C:
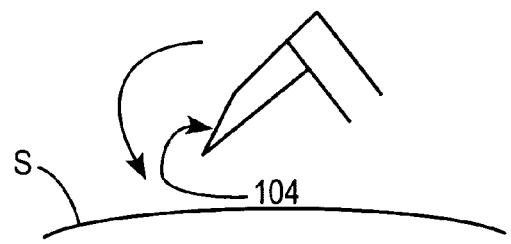
Figure 8D:
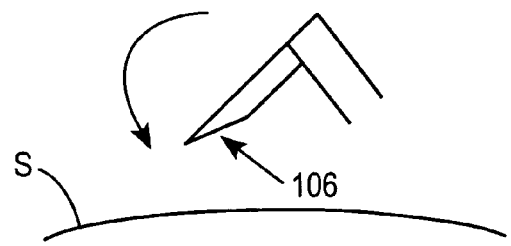

According to the present invention, additional skin penetration element embodiments are envisioned. For example, several possible orientations for one or more bevel(s) formed at the end of a skin penetration element or member, such as a lancet or needle are contemplated. Four such alternatives are illustrated in FIGS. 8A-8D. In the arrangement of FIG. 8A, the bevel(s) 100 of the skin-penetration element or member are oriented facing forward, as illustrated. According to the arrangement of FIG. 8B, the bevel(s) 102 are orient facing the backside of the skin-penetration element or member. In the arrangement of FIG. 8C, the bevel(s) 104 are oriented facing away from the surface of the skin S. According to the arrangement of FIG. 8D, the bevel(s) 106 are oriented facing the surface of the skin S. According to the present invention, when the actuator is chosen that drives the skin penetration member along an arcuate or rotational path, it has been observed that a bevel orientation that faces away from the surface of the skin, or as illustrated in FIG. 8C as an "anti-scoop" configuration, may result in a less visible wound.

Figure 9:
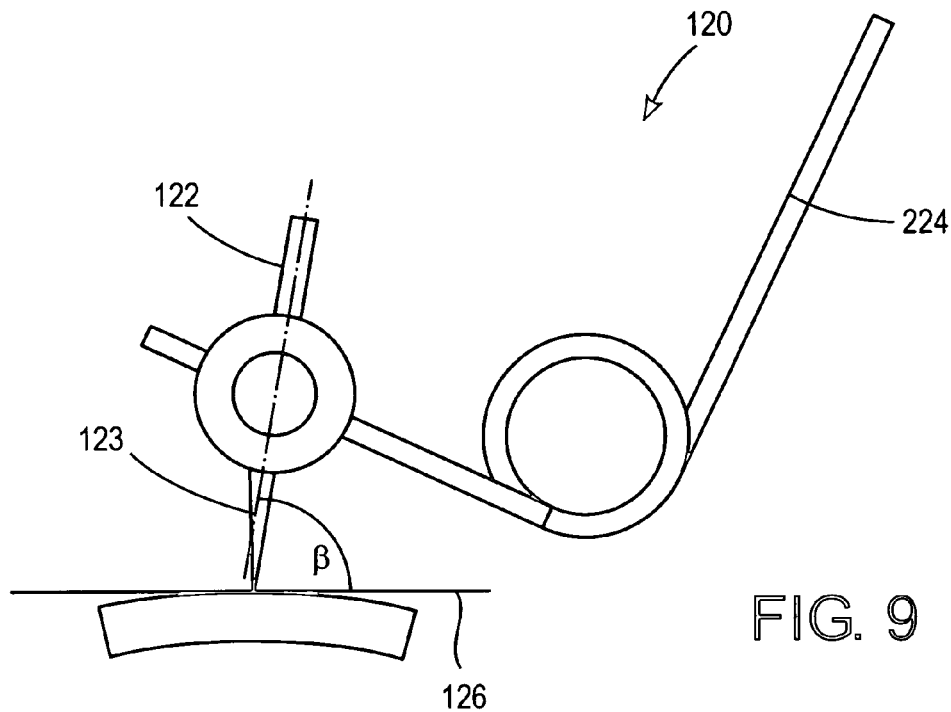
FIG. 9 is a side view of an arrangement including a skin-penetration member configured according to a first optional embodiment.
Figure 10:
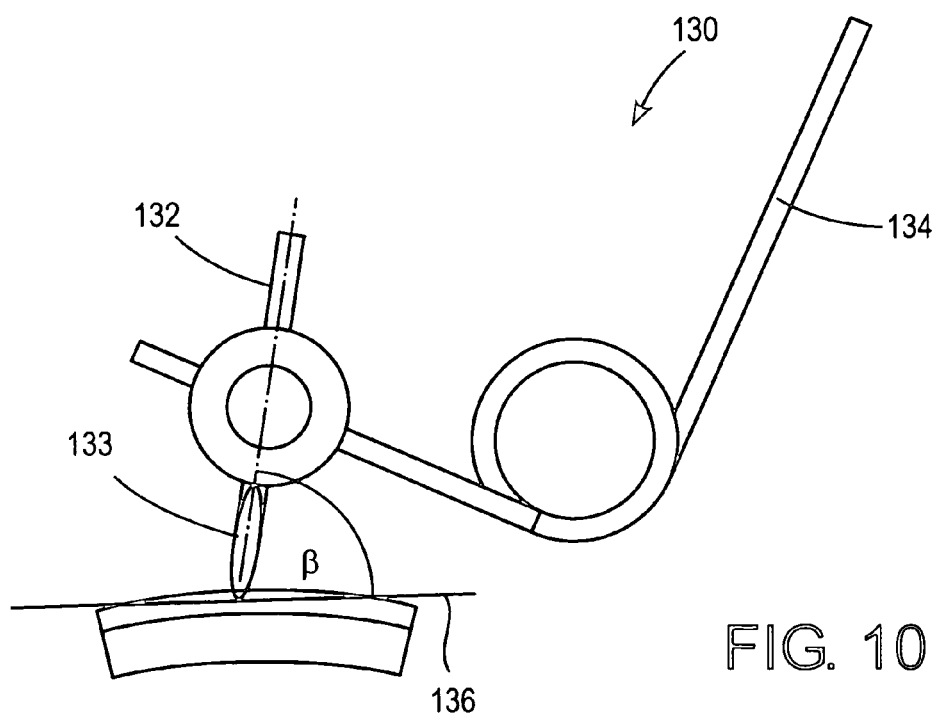
FIG. 10 is a side view of an arrangement including a skin-penetration member configured according to a second optional embodiment.
Figure 11:
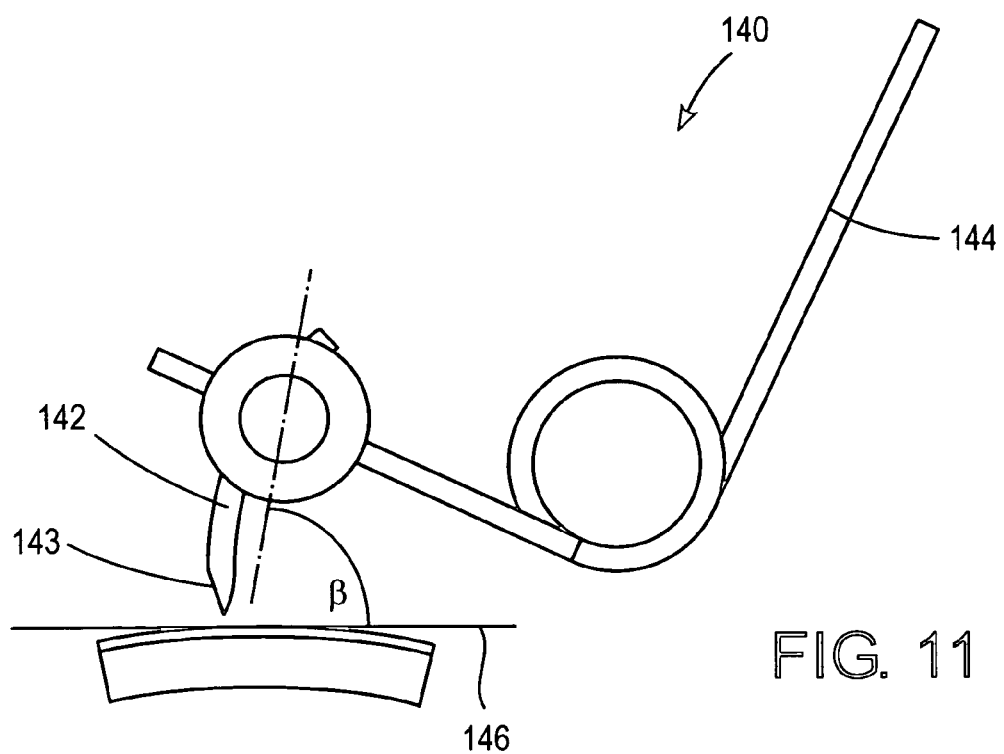
FIG. 11 is a side view of an arrangement including a skin-penetration member configured according to a third optional embodiment.
Figure 12A:
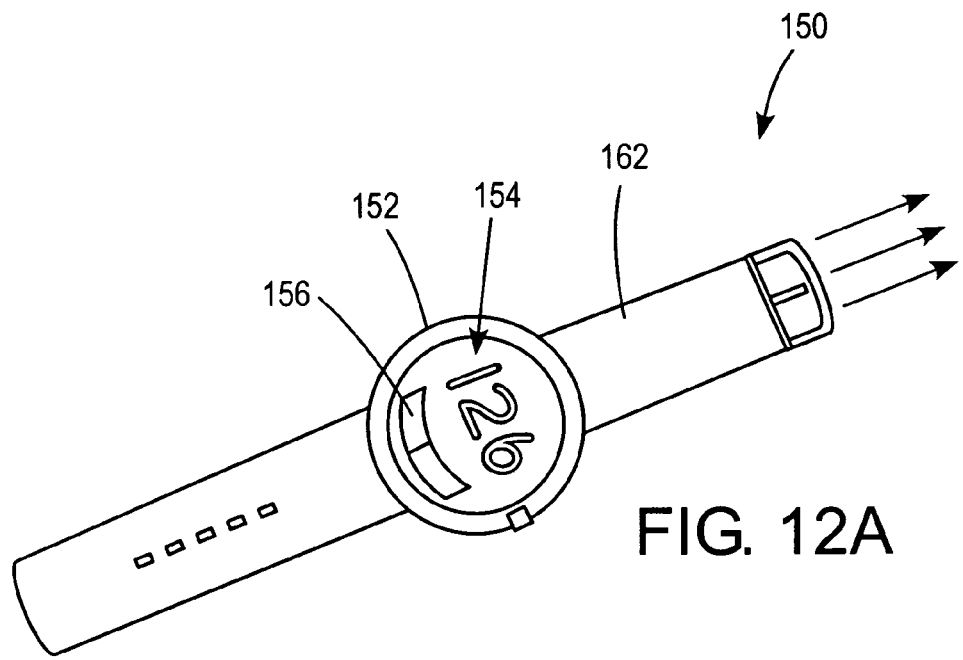
FIG. 12A-12B are top and bottom views, respectively, of an arrangement configured according to an optional embodiment.
Figure 12B:
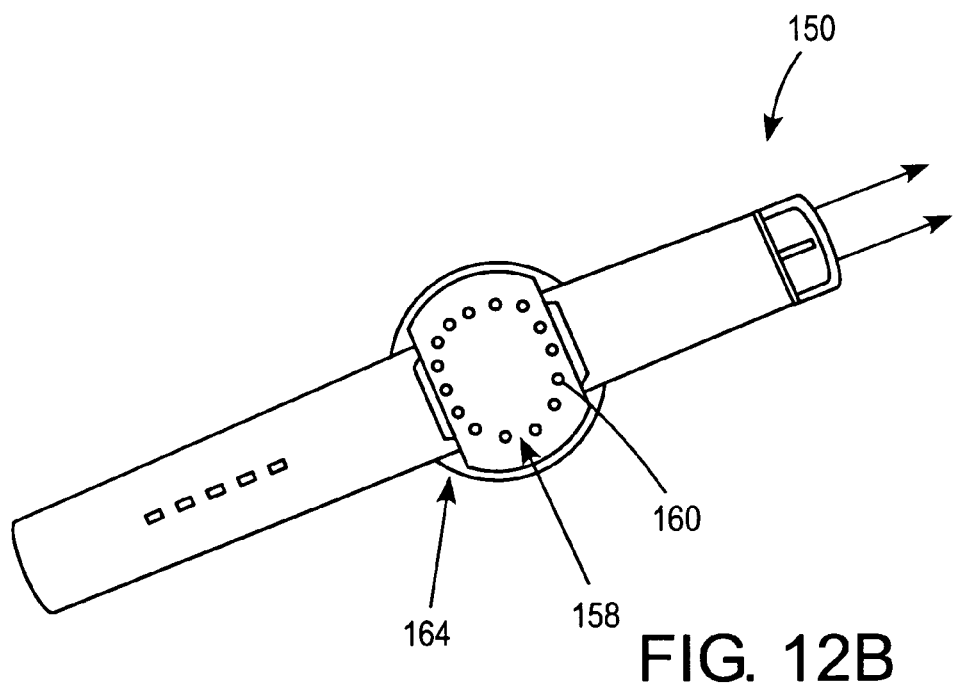

Three additional alternative arrangements for producing a sample of blood or body fluid by piercing the surface of the skin, while minimizing the wound created therein, are illustrated in FIGS. 9-11.

As illustrated in FIG. 9, an arrangement 120 may comprise a skin-piercing element 122, such as a lancet or a hollow needle, which is attached to an actuation member 124. According to the illustrated embodiment, the actuation member is configured to drive the skin-piercing element 122 along an arcuate or rotational path. The a skin piercing element 122 and actuation member 124 can be configured such that the skin piercing element forms an entry angle β of 90°+/−20°. The entry angle being defined, as illustrated in FIG. 9, as the angle formed between the longitudinal axis of the skin piercing element 122 and the plane defined by the surface of the skin 126. Providing the arrangement 120 with an entry angle β as described above has been observed as minimizing wound formation. According to the arrangement 120, the skin piercing element 122 is provided with a bevel 123 that is in the anti-scoop orientation, or facing away from the surface of the skin (see, e.g., FIG. 8C).

According to the arrangement 120, the skin-piercing element 122 and the actuation member 124 are configured and arranged such that the path of travel of the end of the skin piercing element 122 after entry into the skin is not too shallow along its radius of travel. In other words, according to one embodiment, the skin piercing element 122 and the actuation member 124 are configured and arranged such that the path of travel of the end of the skin piercing element 122 after entry into the skin is closer to the perpendicular, or a wider arc, as opposed to a travel path that is more parallel to the surface of the skin 126.

An alternative arrangement 130 is depicted in FIG. 10. The arrangement 130 has the same features and characteristics as the arrangement 120 described above, except for the following distinctions. According to the arrangement 130, a skin-piercing element 132 is provided that has a bevel 133 that is oriented in a "slice" configuration (see, e.g., FIG. 8A). In other words, the bevel 133 is rotated approximately 90° away from the plane defined by the surface of the skin 126.

A further alternative arrangement 140 is depicted in FIG. 11. The arrangement 140 has the same features and characteristics as the arrangement 120 described above, except for the following distinctions. According to the arrangement 140, a skin-piercing element 142 is provided that has a generally arcuate or curved shape. A skin-piercing element 142 having this arcuate or curved configuration advantageously prevents in-plane forces with the skin as it travels along an arcuate or curved path. The skin piercing element 142 may be provided with a radius of curvature that approximates the radius of curvature if its path of travel when driven by the actuation member 144. The skin-piercing element 142 has a bevel 143 that is oriented in an anti-scoop orientation, or facing away from the surface of the skin (see, e.g., FIG. 8C).

While a wearable integrated meter has several advantages over current technology it is understood that there may be times when the user is either unable or would prefer not to wear the integrated meter. Examples of such situations include during exercise, swimming, sleeping, or when social situations where the style of the watch may be inappropriate. Thus, the present invention also advantageously comprises a wearable meter that can be converted into a handheld meter.

The compact size of the integrated devices of the present invention allows the user to carry everything necessary to complete a test in a small pocket. For example, if a user needed to attend a formal dinner they most likely will not have space to carry all of the components associated with currently available glucose testing systems. These users will likely take a health risk and ignore testing during the event. The size of the integrated devices of the present invention allows the user to carry the entire device in their pocket and test discreetly in a restroom, or even beneath the table on their lap.

Integrated wearable devices according to the present invention that can be converted to a hand held device also allow the user to test at a digit or the fingertip if needed or desired. While testing at an alternate site such as the wrist is safe and accepted during certain hypoglycemic incidents, it is still advantageous for the user to be able to test at the finger to get an even more accurate glucose reading. Also, regardless of increased pain and other factors, some users may prefer to test at a digit or the fingers regularly and only occasionally wear the device for convenience. The present invention provides for such usage.

The following features facilitate usage of convertible hand held integrated devices formed according to the present invention. Thus, an integrated device formed according to the present invention may also include one or more of the following features.

According to one embodiment, the device is provided with a footprint comprising a single opening for testing. The user operates the device upside down by placing their fingertip on top of the footprint, or the user operates the device face side up and locates their fingertip under the footprint. For upside-down operation the device may have alerts that are not visible, for example tactile (vibrations, heat, etc.), or audible alerts. These alerts can be used to inform the user that a test is about to begin and to notify the user that a test is complete. To further simplify operation the device can have an "on-demand finger test" trigger on the device. This trigger will allow the user to initiate a test without having to look at the top face of the device. For example, the user may remove the watch from their wrist press a button or combination of buttons that place the system into finger test mode. In this state, the finger test trigger would be in the active state. The user could then turn over the device and use it without looking at the topside of the device. Potential triggers include buttons, pressure sensors, capacitive sensors and other commonly known input mechanisms. It is also possible to have the finger trigger activate as soon as it detects that a finger is placed on it for a set period of time. This will eliminate the need to change the device to "finger mode", thereby simplifying the testing process. Another embodiment comprises a footprint having multiple openings that can be used to complete a finger test, and allows the user to complete a test while still looking at the top face of the device. With this construction, the user will have to correctly identify the opening upon which to place their finger. Several features are contemplated to assist with testing in this manner.

The top face of the device can have features that point the user to the proper location for the current test. Such features can be visible indicators, such as LED's, around the perimeter of the device that correspond to each opening in the footprint. For example, before a test the corresponding LED will illuminate, guiding the user to the correct position under the device.

Visual indicators, such as the above-mentioned LED's, can also be used below the device to illuminate the targeted sampling site and allow the user to correctly position the device. These LED's would have the added benefit of allowing the user to correctly place the device in a poorly lit environment. Another feature for guiding the user to the correct location for a test is to have the display of the device display an arrow that points to the correct position or opening in the footprint for a test.

Each footprint can include a sensor (pressure, switch, capacitive, thermal, etc.) to determine that a finger is present. The device would be able to fire any of the actuators at anytime, so when the user places their finger under an opening in the footprint, an actuator would fire and a test would be completed. If the user placed their finger under an opening in the footprint that had already been used, the device could detect that and tell the user to move their finger to another site.

According to a further alternative, certain openings in the footprint may be reserved for finger testing. These openings would be easily identifiable by site or touch, allowing the user to accurately position their finger for a test.

In one embodiment, a device such as the one illustrated in FIG. 1A-1B can be converted from a wearable to a handheld device by simply opening the strap that attaches the device to the user's wrist. That is this device 10 is designed such that the functional portion 14 of the device 10 can operate without being attached to the user. For instance if the device 10 was designed to be worn at the wrist, and the user wanted to use the device as a handheld monitor, the user would simply open the band 12 holding the device 10 on at the wrist and place the functional portion 14 of the device 10 on the location they wished to test, forearm, finger, palm, thigh, etc. The user would then be able to reattach the device to their wrist, or place the device 10 in a pocket or other location until needed again.

Alternative embodiments of the present invention are illustrated in FIGS. 12A-15. As illustrated therein, an arrangement 150 generally comprises an integrated device 152 of the type described above. The integrated device 152 includes a top face 154 which may include a display and one or more buttons 156. The integrated device 152 also comprises a bottom face 158 defining a footprint comprising one or more openings 160 through which a skin-piercing element may extend. An attachment element, such as a strap 162 may be provided to attach the device to a suitable location on the wearer, such as the wrist. A quick release mechanism 164 is provided which permits removal of the attachment element 162 from the integrated device 152. Any suitable quick release mechanism 164 is contemplated.

Figure 13A:
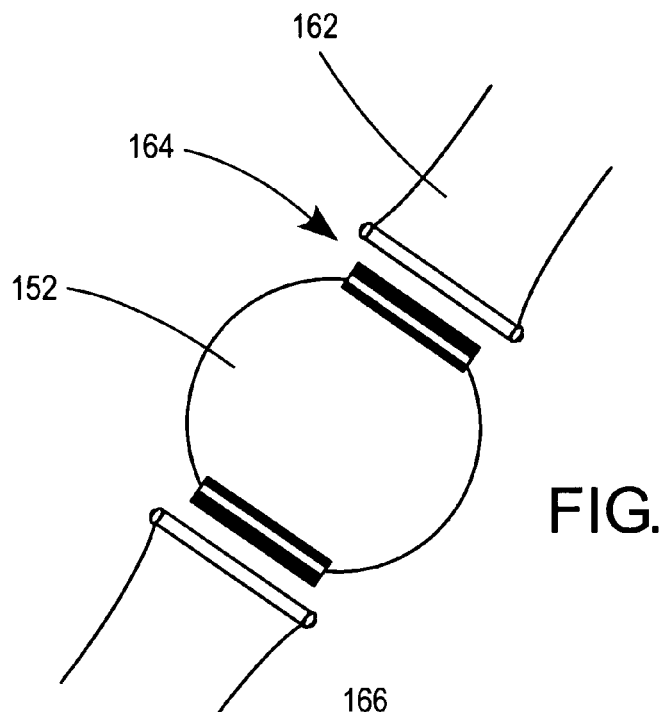
FIGS. 13A-13C are bottom and side views, respectively, of an arrangement configured according to an alternative embodiment.
Figure 13B:
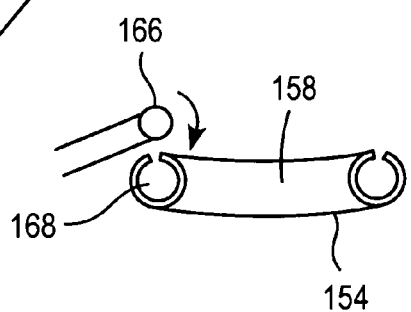
Figure 13C:
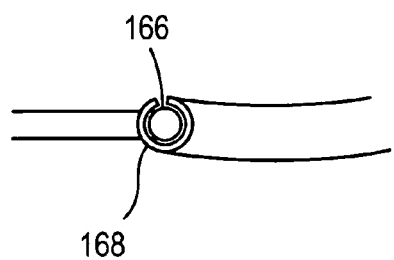

One such suitable quick release mechanism 164 is illustrated in FIGS. 13A-13C. According to the illustrated embodiment, the quick release mechanism 164 comprises a generally cylindrically shaped portion 166 which is received within a generally C-shaped portion 168 in a snap-fit type connection.

Figure 14:
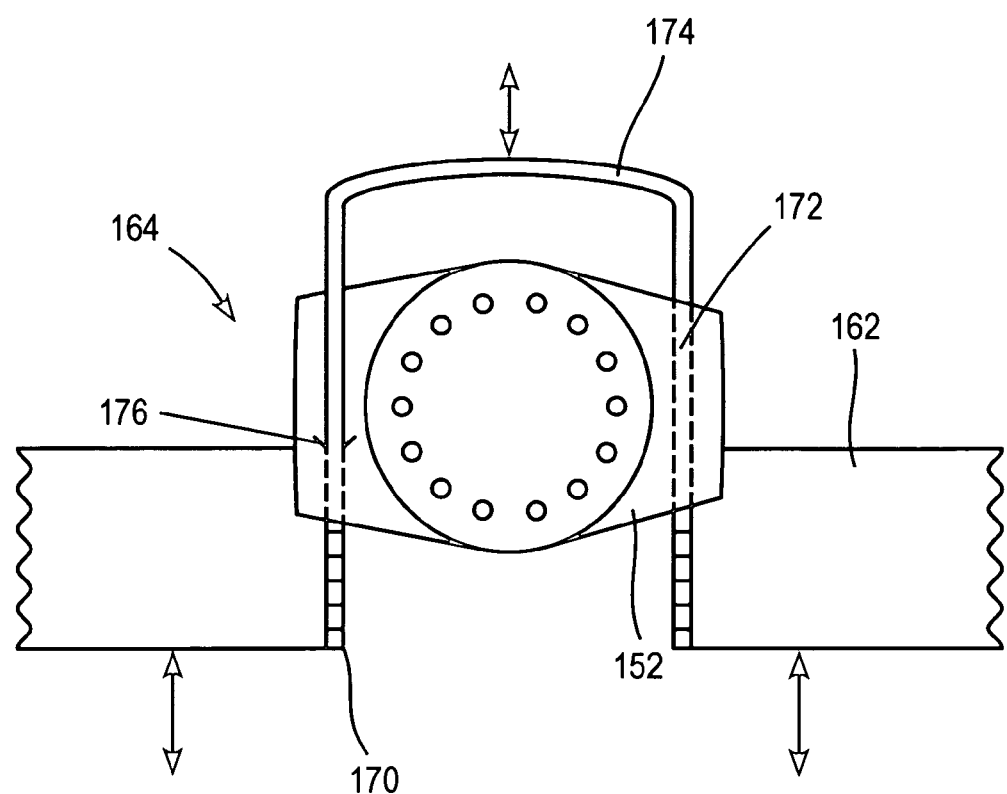
FIG. 14 is a bottom view of an arrangement formed according to a further alternative embodiment.

Another alternative quick release mechanism is illustrated in FIG. 14. As illustrated therein, the quick release mechanism 164 comprises a hollow generally cylindrically shaped portion 170 disposed on the ends of the band 162. The portions 170 on the ends of the attachment means or band 162 are concentrically received within complimentary hollow generally cylindrically shaped portions 172 disposed on the ends of the integrated device 152. A clip 174 is then inserted within the cylindrically shaped portions 170 of the band 162. The clip 174 includes a locking feature 176 disposed at one or more ends of the clip 174 for releasably securing the clip 174 once inserted all the way through the cylindrical portions 176. The locking feature 176 may take any suitable form, such a collapsible detent.

Figure 15:
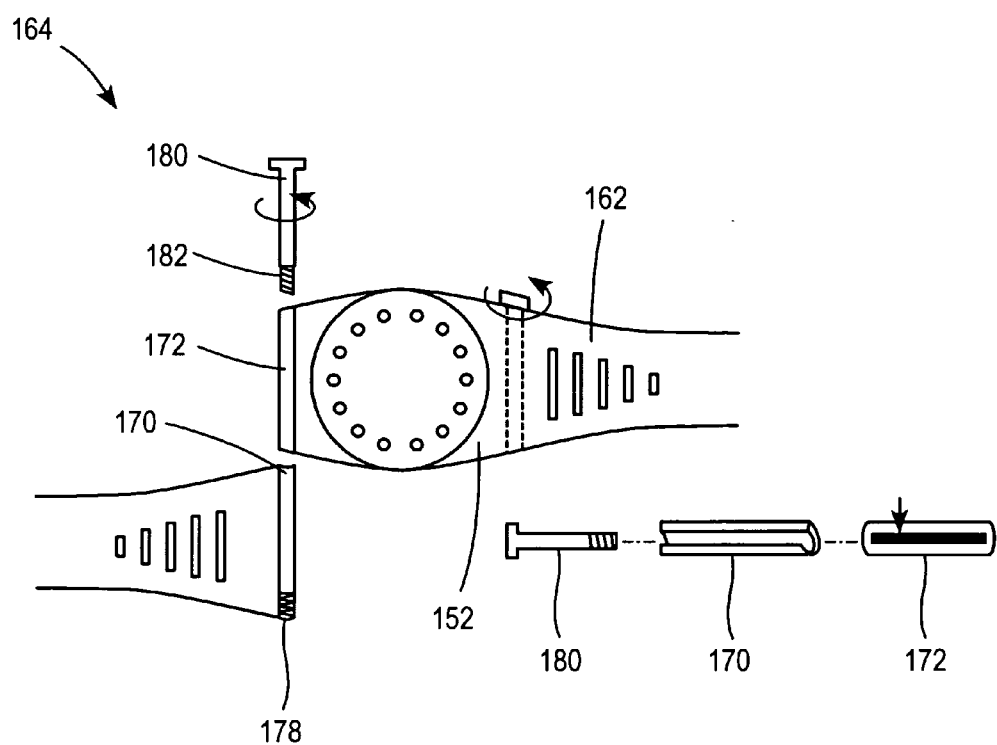
FIG. 15 is a bottom view of an arrangement formed according to yet another optional embodiment.

According to a further embodiment, the quick release mechanism 164 may take the form of that illustrated in FIG. 15. As illustrated in FIG. 15, the hollow cylindrical portions 170 disposed at the ends of the band 162 are provided with a threaded end 178. A pin 180 having a threaded end 182 is received within hollow cylindrical portions 172 provided at the ends of the integrated device 152, as well as the hollow cylindrical portions 170 disposed at the ends of the band 162. A pin 180 is then rotated such that the threaded end 182 thereof mates in threaded engagement with the threaded end 178 of the hollow cylindrical portions 170, thereby securing the integrated device 152 to the band 162 in a releasable fashion.

Figure 16:
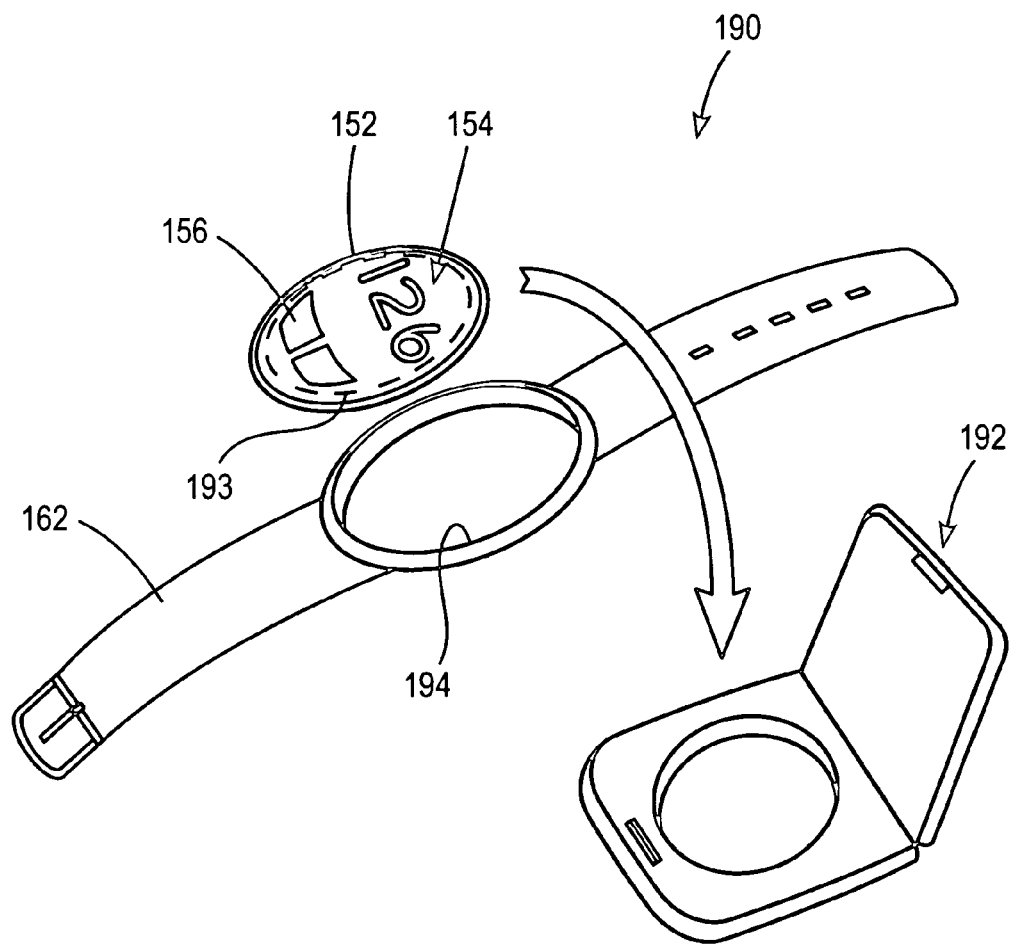
FIG. 16 is a perspective view of another embodiment of an arrangement formed according to the present invention.

An arrangement constructed according to a further alternative embodiment of the present invention is illustrated in FIG. 16. As illustrated therein, the arrangement 190 includes a separate carrying case 192 which is configured to receive the integrated device 152, once removed from the attachment element or band 162. It should be understood that the case 192 may also be utilized with any of the previously described embodiments. The arrangement 190 further includes an alternative means for separately retaining the integrated device 152 and the band 162. As illustrated therein, the band 162 formed as a one piece member comprising a recess or pocket 194 disposed therein for housing the integrated device 152 in a releasable manner. Any suitable mechanism may be provided to releasably secure the integrated device 152 within the recess or pocket 194. Suitable mechanisms include a friction fit, snaps, detents, and releasable fasteners. The provision of a case 192 according to the present invention advantageously protects the footprint, and the integrated device 192 as a whole, from damage. The case also may help to prevent bio hazardous materials (e.g., blood) from spreading if the device is laid on a surface. An additional benefit of the case 192 that it may contain an additional power source, motor, or other components that may assist in operation of the integrated device 152.

As an alternative to the separate case 192, a similar protective feature or features may be integrated into the device 152. For example, the device 152 is separated from the band 162, the device 152 may be provided with a rotatable plastic shield 193, which can be rotated into a position which covers the openings 160 in the footprint 158. When the user is ready to use the device, the plastic shield 193 is rotated again until the openings 160 and footprint 158 are accessible. According to a further alternative, a plastic shield 193 can be configured such that it will cover all but one of the openings 160. This enables the entire device to be evacuated and the remaining open footprint sealed against the user's skin, such as by application of a vacuum. This embodiment advantageously facilitates the use of a vacuum in conjunction with sampling, and eliminates the need to isolate each individual chamber against vacuum leaks.

Figures 17A, 17B:
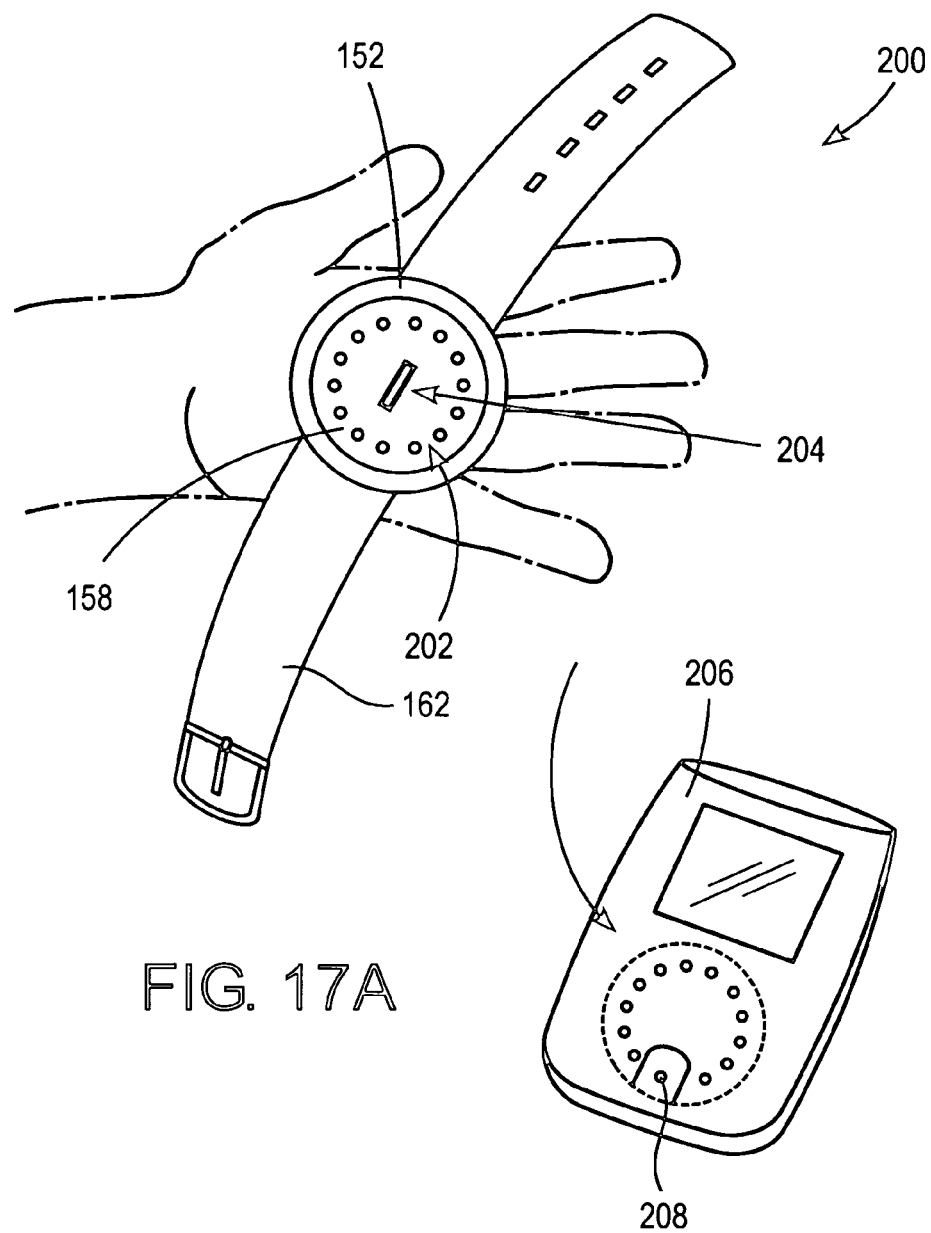
FIG. 17 is a perspective view of yet another embodiment of an arrangement formed according to the present invention.

A further alternative embodiment of the present invention is illustrated in FIGS. 17A-17B. As illustrated therein, the arrangement 200 comprises an integrated device 152 of the type described above which includes a housing 202. The housing 202 is separable from the attachment element 162 via any suitable mechanism, such as the illustrated recess 204 which is designed to receive a coin or tool therein which is then twisted by the user to separate the housing 202 from the attachment element 162. The housing 202 can then be inserted into a separate handheld device 206. According to this embodiment, the housing 202 contains the skin-piercing elements, reagents, and other components. Both the reusable portion of the integrated device 152, as well as the handheld unit 206 contain controls, a display, power supply, optics, and other components necessary to carry out the test. According to this arrangement, a user can buy a number of disposable housing or units 202 which are usable in either a discrete wearable device, or a handheld device.

In order to facilitate use of the handheld device for finger testing, the handheld device 206, or the separate case 202, may be provided with a feature for accurately positioning the finger for testing such as footprint area 208 which may include a groove or channel in which the user can lay their finger. The device can be designed such that the unit then rotates until an available test site is aligned with the opening disposed in the recess or channel in registry with the users finger.

Certain modes of operation of an integrated device or meter of the type described herein are also contemplated by the present invention.

Before any testing can occur the user opens all the packaging and inserts a disposable unit into the wearable or hand held device. The disposable portion or unit may be attached via several mechanical methods including threads, screws, snaps, etc.

After a disposable is loaded, the device prepares itself to initiate a test. Preparations may include reading the calibration codes on the disposable portion, measuring a controlled calibration fluid, and/or other self checks. During startup the device may also prompt the user to schedule test intervals. The user should now place the device on their body, possibly the wrist, optionally using an attachment means.

When it is time for a scheduled test, or the user requests a test, the device begins test preparations. The device may give user an indication that a test is imminent; the indication may be visual, audible, tactile or a combination of indicators. If necessary, the device will index to the next available test setup location. The indexing may be via a motor driven mechanism or stored mechanical energy. The device may now cock the skin piercing member. The device may now test to ensure skin contact. The device may now initiate a catalyst process. Catalyst processes are intended to increase fluid sample availability and production at the sampling site.

At this point a trigger releases the actuation mechanism and drives the skin piercing member into the skin.

After piercing the skin the device begins to transport the fluid or blood to the quantification media. Once the sample arrives at the quantification media, a reaction occurs. This reaction is measured to produce an analyte reading. Once a sufficient sample volume is delivered to the quantification media, the catalyst process may be terminated. The device may now output a reading to the user. When it is time for the next test the process is repeated. If the testing fails, the device may automatically repeat a test. The device will inform the user of remaining number of tests. When all tests are used the device will prompt user to load a fresh disposable unit.

Figure 18:
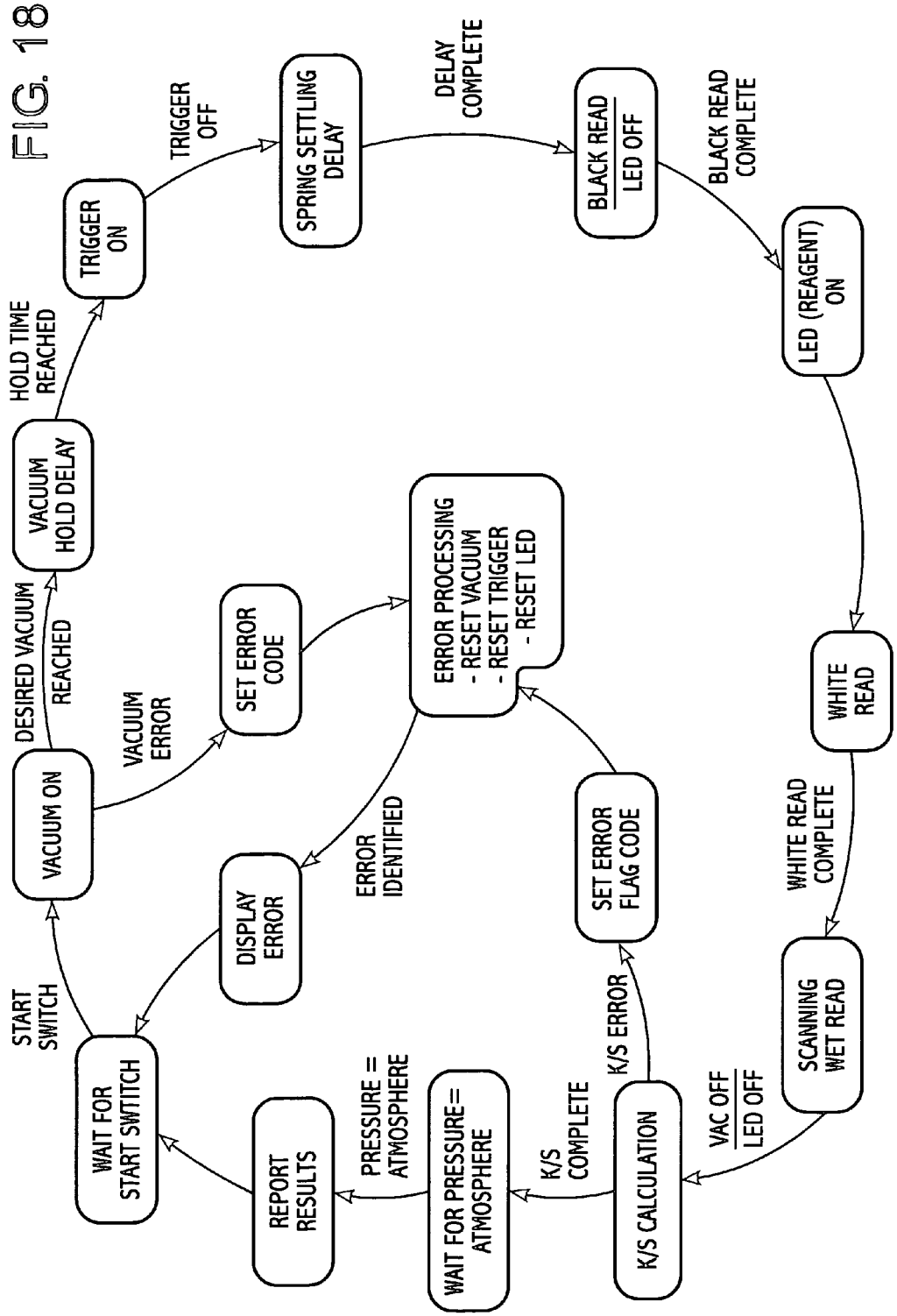
FIG. 18 is a schematic state diagram illustrating one possible mode of operation of an integrated device formed according to the present invention.

According to one illustrative embodiment of the present invention, an integrated device is operated according to the state diagram contained in FIG. 18. At least the following operations are illustrated therein.

1) A start switch closure starts off the sequence.
2) The vacuum pump turns on.
3) When the vacuum set point is reached, the vacuum is maintained for a vacuum hold period (nominally set to 5 seconds). This catalyst increases blood production to a practical/usable amount.
4) The trigger releases the sharp immediately after the "vacuum hold" is completed.
5) A spring settling delay state allows the spring to settle in a fixed position before the CMOS sensor can read parameters required for K/S calculation and subsequent glucose levels. This delay does not start until the trigger is released. The reasons for this is that the release of the trigger could potentially move the assay pad and produce an unwanted spatial error on the black or white reference signals.
6) A black read is performed, typically with the reagent LED illumination extinguished.
7) The reagent LED illumination is then turned on.
8) A white read is done.
9) The scanning wet read puts the CMOS image results into a database.
10) The vacuum is released upon acquisition of a sufficient volume of sample detected by the CMOS image detector.
11) A K/S and/or glucose concentration calculation then takes place.
12) The reporting state displays the result of the above calculation or any errors that may exist.
13) Several errors can be trapped, and in most cases, abort the sequence. Such errors include things like insufficient vacuum, loss of vacuum, unexpected white read value and other user aborts.
14) The glucose concentration is not displayed until the chamber is within 0.5 in. Hg. This keeps blood from blowing unnecessarily into the chamber, thus requiring a major cleanup.
15) The last state simply waits for the next start button closure.

It should be understood, that consistent with the principles of the present invention and in connection with the exemplary mode of operation illustrated in FIG. 18, one or more of the above-described actions may be omitted, modified, or the order in which they are performed can be altered from the illustrated embodiment described above. In addition, one or more additional actions other than those listed above can be added to the illustrated embodiment.

An exemplary body fluid sampling and analysis methodology or technique, which may be utilized in conjunction with any of the above-mentioned devices or integrated meters, but is not necessarily limited thereto, is described as follows.

A user loads a fresh disposable cartridge containing a plurality of skin penetration members and analysis sites into an integrated meter. The integrated meter then reads calibration data contained in or on the cartridge. This data can be read in any suitable manner. For example, a bar code may be placed on the cartridge which can be optically read by the optical assembly contained within the meter. The integrated meter then selects the proper lookup table or algorithm to calculate an aggregate glucose measurement taking into consideration the calibration data. The meter may then place itself in a ready mode waiting for a trigger to initiate sampling and testing. The user then either manually presses a button or trigger to initiate sampling and analysis, or the device verifies that it is properly positioned on the skin of the user and ready to begin the sampling and analysis procedure. Suitable sensors to accomplish this include optical, capacitive or pressure sensors. The device then initiates a catalyst which acts to facilitate the expression of body fluid. According to one alternative embodiment, the catalyst is an inflatable member that exerts pressure on a digit. Alternatively, the catalyst is vacuum pressure which generates suction at the sampling site. Sensors present in the meter may be used to monitor and control the positive or negative pressure of the catalyst. After achieving a target pressure for a desired period of time, the skin penetration member (e.g., a hollow needle) is actuated and driven into the skin of the user to create a wound site. The skin penetration member comes to rest in or directly on the wound created at the sampling site where it is in the desired position for collecting a sample of body fluid expressed from the wound. The integrated meter may further include a mechanism for detecting a whether a sufficient amount of sample has been expressed. Details of such suitable detection techniques are described in detail in U.S. Pat. No. 7,052,652, entitled ANALYTE CONCENTRATION DETECTION DEVICES AND METHODS, the entire content of which is incorporated herein by reference. Once the desired amount of body fluid has been obtained, the catalyst may be deactivated. A sample of body fluid is in fluid communication with a device or mechanism which creates a detectable signal upon reaction within analyte present in the sample body fluid. For example, one such suitable mechanism is a absorbent pad containing a chemical reagent which, upon reaction with the analyte produces a reaction spot which can be optically detected. An optical assembly which is in optical communication with the above described signal generating mechanism is utilized to detect the signal created via reaction with the analyte and communicate the signals to supporting electronics contained within the meter. The concentration of a target analyte (e.g., glucose) can then be calculated using these signals as a basis. Additional factors may be considered during these calculations, such as the sample size, levels of other substances contained in the sample (e.g. hematocrit), etc. Such optional calculation techniques are described in further detail in U.S. patent application Ser. No. 11/239,122, entitled ANALYTE DETECTION DEVICES AND METHODS WITH HEMATOCRIT/VOLUME CORRECTION AD FEEDBACK CONTROL, the entire content of which is incorporated herein by reference. These calculations quantify the amount of analyte contained in the sample body fluid. This quantity is displayed on a suitable display contained within the meter which can be easily read by the user. The integrated meter then automatically indexes the disposable cartridge to present a fresh unused skin penetration member which will be utilized to perform the next sampling and analysis event.

Numbers expressing quantities of ingredients, constituents, reaction conditions, and so forth used in this specification are to be understood as being modified in all instances by the term "about". Notwithstanding that the numerical ranges and parameters setting forth, the broad scope of the subject matter presented herein are approximations, the numerical values set forth are indicated as precisely as possible. Any numerical value, however, inherently contains certain errors necessarily resulting from the standard deviation found in their respective measurement techniques. None of the elements recited in the appended claims should be interpreted as invoking 35 U.S.C. §112, 16, unless the term "means" is explicitly used.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

We claim:

1. An integrated body fluid sampling and analysis device, the device comprising:
   a housing, the housing containing a plurality of body fluid sampling and analysis sites, each of the sites comprising a skin-penetration member in the form of a needle comprising a lumen, and a torsional spring actuator, the torsional spring actuator comprising a first leg, and a second leg moveable relative to the first leg upon release of elastic energy stored in the torsional spring actuator, the skin-penetration member connected to the moveable second leg so as to drive the skin-penetration member into the skin of a user and to act as a guide locating an end of the needle in the body fluid due to the release of the elastic energy and so as to draw the body fluid into the lumen of the needle.

2. The device of claim 1, wherein the device further comprises a body attachment element comprising a band.

3. The device of claim 2, wherein the device further comprises a quick release mechanism connecting the housing and the body attachment element, the quick-release mechanism comprises a generally C-shaped portion, and a generally cylindrically-shaped portion received within the generally C-shaped portion with a snap-fit type connection.

4. The device of claim 2, wherein the device further comprises a quick release mechanism connecting the housing and the body attachment element, the quick-release mechanism comprises a generally hollow portion disposed on the body attachment element received within a complementary generally hollow portion disposed on the housing, and a clip inserted into the generally hollow portion disposed on the housing, the clip comprising a locking feature disposed at an end of the clip.

5. The device of claim 4, wherein the locking feature comprises a collapsible detent.

6. The device of claim 2, wherein the device further comprises a quick release mechanism connecting the housing and the body attachment element, the quick-release mechanism comprises a generally hollow portion disposed on the body attachment element received within a complimentary generally hollow portion disposed on the housing, the generally hollow portion disposed on the body attachment element comprising a threaded end and a pin received therein, the pin comprises a threaded end mating with the threaded end of the end of the hollow portion.

7. The device of claim 2, wherein the device further comprises a quick release mechanism connecting the housing and the body attachment element, the quick-release mechanism comprises a pocket formed in the body attachment element receiving the housing therein in a releasable manner in the form of one or more of: a friction fit, snaps, detents or releasable fasteners.

8. The device of claim 1, further comprising a disposable portion and a reusable portion.

9. An integrated body fluid sampling and analysis device, the device comprising:

a housing, the housing containing a plurality of body fluid sampling and analysis sites, each of the sites comprising a skin-penetration member in the form of a needle comprising a lumen, and a torsional spring actuator, the torsional spring actuator comprising a first leg, and a second leg moveable relative to the first leg upon release of elastic energy stored in the torsional spring actuator, the skin-penetration member connected to the moveable second leg so as to drive the skin-penetration member into the skin of a user and to act as a guide locating an end of the needle in the body fluid due to the release of the elastic energy and so as to draw the body fluid into the lumen of the needle, wherein the torsional spring actuator is configured to accelerate the end of the skin-penetration member along a curved or rotational path of travel of the second leg of the torsional spring actuator due to the release of the elastic energy.

10. The device of claim 1, wherein each of the sampling and analysis sites further comprise a trigger configured to release the actuator.

11. The device of claim 1, wherein the skin-penetration member comprises a hollow needle.

12. The device of claim 1, wherein each of the body fluid sampling and analysis sites comprises an assay pad, the assay pad comprising a chemical reagent for producing a detectable signal upon reaction with a target analyte.

13. The device of claim 12, wherein the signal is optically detectable, and the arrangement further comprises a detector configured to detect the signal.

14. The device of claim 1, wherein the analysis sites are arranged about a circle in a circumferential manner.

15. The device of claim 1, wherein the analysis sites are oriented in the radial direction.

16. The device of claim 1, wherein the sampling and analysis sites are oriented in a linear manner.

17. The device of claim 1, wherein the skin-penetration member comprises a bevel turned 90° away from the surface of the skin of a user.

18. The device of claim 1, wherein the skin-penetration member comprises a bevel facing toward the surface of the skin of a user.

19. The device of claim 1, wherein the skin-penetration member comprising a bevel facing away from the surface of the skin of a user.

20. The device of claim 1, wherein the housing further comprises a display and one or more buttons.

21. The device of claim 1, wherein the housing further comprises a footprint, the footprint comprising one or more openings in registry with one or more sampling and analysis sites.

22. The device of claim 1, further comprising a case configured to receive the housing therein.

23. The device of claim 22, wherein the case comprises a display.

24. The device of claim 8, wherein the disposable portion comprises a disposable cartridge.

25. An arrangement comprising:
a housing containing one or more components configured for at least one of body fluid sampling or analysis; and
at least one skin-penetration member comprising a needle, the needle comprising a lumen, and
at least one torsional spring actuator, the at least one torsional spring actuator comprising a first leg, and a second leg moveable relative to the first leg upon release of elastic energy stored in the at least one torsional spring actuator, the skin-penetration member connected to the moveable second leg so as to drive the needle into a surface of the skin along a path traveled by the second leg due to the release of the elastic energy and to act as a guide locating an end of the needle in the body fluid so as to draw the body fluid into the lumen of the needle.

26. A method of quantifying the presence or concentration of an analyte contained in a sample of body fluid the method comprising:
providing a housing with one or more components configured for at least one of body fluid sampling or analysis, the components comprising at least one skin-penetration member and at least one torsional spring actuator comprising a first leg, and a second leg moveable relative to the first kg;
applying the housing to a surface of the skin; and
piercing the skin with the at least one skin-penetration members;
wherein the at least one skin-penetration member is provided in the form of a needle comprising a lumen, wherein the needle is attached to the second leg, and the needle is driven to pierce the skin by the at least one torsional spring actuator and the needle is guided by the second leg of the at least one torsional spring actuator so as to locate an end of the needle in the body fluid so as to draw the body fluid into the lumen of the needle, and wherein the needle is not retracted prior to quantifying the presence or concentration of an analyte in the sample of body fluid.

27. The arrangement of claim 25, wherein the path defined solely by the path traveled by the moveable second leg of the actuator is a curved or rotational-path.

28. The arrangement of claim 27, wherein the at least one torsional spring actuator comprises a neutral rest position following the release of elastic energy, and wherein the neutral rest position is configured to position the end of the needle in an opening formed in the surface of the skin by the needle.

29. The arrangement of claim 27, wherein the at least one torsional spring actuator guides the skin-penetration member along a path such that the skin-penetration member forms an entry angle between a longitudinal path of the skin penetration member and the surface of the skin of 90°+/−20°.

* * * * *

UNITED STATES PATENT AND TRADEMARK OFFICE
CERTIFICATE OF CORRECTION

| | |
|---|---|
| PATENT NO. | : 8,382,681 B2 |
| APPLICATION NO. | : 11/529612 |
| DATED | : February 26, 2013 |
| INVENTOR(S) | : Raul Escutia et al. |

It is certified that error appears in the above-identified patent and that said Letters Patent is hereby corrected as shown below:

Claim 26, column 18, line number 26, replace the word "kg" with --leg--

Signed and Sealed this
Fourteenth Day of May, 2013

Teresa Stanek Rea
*Acting Director of the United States Patent and Trademark Office*